US012672626B1

(12) United States Patent
Cook et al.

(10) Patent No.: US 12,672,626 B1
(45) Date of Patent: Jul. 7, 2026

(54) CHICKPEA VARIETY 'NC-001'

(71) Applicant: NuCicer, Inc., Davis, CA (US)

(72) Inventors: Douglas Cook, Davis, CA (US);
Brendan Riely, Davis, CA (US)

(73) Assignee: NuCicer, Inc., Davis, CA (US)

( * ) Notice: Subject to any disclaimer, the term of this patent is extended or adjusted under 35 U.S.C. 154(b) by 194 days.

(21) Appl. No.: 18/374,146

(22) Filed: Sep. 28, 2023

Related U.S. Application Data

(60) Provisional application No. 63/411,236, filed on Sep. 29, 2022.

(51) Int. Cl.
  *A01H 6/54* (2018.01)
  *A01H 5/10* (2018.01)
(52) U.S. Cl.
  CPC ................. *A01H 6/54* (2018.05); *A01H 5/10* (2013.01)
(58) Field of Classification Search
  CPC .................................... A01H 6/54; A01H 5/10
  See application file for complete search history.

(56) References Cited

U.S. PATENT DOCUMENTS

| | | | |
|---|---|---|---|
| 4,769,061 | A | 9/1988 | Comai |
| 4,810,648 | A | 3/1989 | Stalker |
| 4,975,374 | A | 12/1990 | Goodman et al. |
| 5,364,471 | A | 11/1994 | Czuchajowska et al. |
| 5,777,196 | A | 7/1998 | Hall |
| 5,948,957 | A | 9/1999 | Chapko et al. |
| 5,959,185 | A | 9/1999 | Streit et al. |
| 5,969,212 | A | 10/1999 | Getschman |
| 5,973,234 | A | 10/1999 | Mueller et al. |
| 5,977,445 | A | 11/1999 | Soper et al. |
| 7,622,632 | B2 | 11/2009 | Ursin et al. |
| 8,142,832 | B2 | 3/2012 | Daek et al. |
| 8,557,321 | B2 | 10/2013 | Segall et al. |
| 8,563,071 | B2 | 10/2013 | Schweizer et al. |
| 9,370,200 | B2 | 6/2016 | Gibbons et al. |
| 10,039,306 | B2 | 8/2018 | Vrljic et al. |
| 10,143,226 | B1 | 12/2018 | Foster et al. |
| 10,390,544 | B2 | 8/2019 | Motoyama et al. |
| 10,834,941 | B2 | 11/2020 | Spinelli et al. |
| 2003/0135879 | A1 | 7/2003 | Weeks et al. |
| 2008/0260929 | A1 | 10/2008 | Ursin et al. |
| 2016/0309743 | A1 | 10/2016 | Spinelli et al. |
| 2018/0042278 | A1 | 2/2018 | Brahimsha et al. |
| 2019/0037893 | A1 | 2/2019 | Ajami et al. |
| 2019/0045809 | A1 | 2/2019 | Lee et al. |
| 2020/0390131 | A1 | 12/2020 | Reifen et al. |
| 2021/0022352 | A1 | 1/2021 | Oladiwura |
| 2021/0051975 | A1 | 2/2021 | Shmulewitz et al. |

FOREIGN PATENT DOCUMENTS

| | | |
|---|---|---|
| EP | 0242246 A1 | 10/1987 |
| EP | 0333033 A1 | 9/1989 |
| EP | 0616644 B1 | 9/1994 |
| EP | 1656449 B1 | 5/2006 |
| WO | WO-1991013972 A1 | 9/1991 |
| WO | WO-1994000992 A1 | 1/1994 |
| WO | WO-2023242831 A1 | 12/2023 |

OTHER PUBLICATIONS

Canadian Food Inspection Agency—NC-001_2025 (Year: 2025).*
Saxena et al (An Integrated Genomic Approach for Rapid Delineation of Candidate Genes Regulating Agro-Morphological Traits in Chickpea. DNA Research 21, 695-710, 2014) (Year: 2014).*
Perez-Rial et al (Phenotypic and genetic characterization of a near-isogenic line pair: insights into flowering time in chickpea. BMC Plant Biology. P1-21, 2024) (Year: 2024).*
Mallikarjuna et al (Molecular Mapping of Flowering Time Major Genes and QTLs in Chickpea (*Cicer arietinum* L.) Frontiers in Plant Science. 1-10, 2017) (Year: 2017).*
Top Crop Manager_2014 (Year: 2014).*
Abe et al., (1987). "Molecular cloning of a cysteine proteinase inhibitor of rice (oryzacystatin). Homology with animal cystatins and transient expression in the ripening process of rice seeds," J. Biol. Chem., 262:16793-16797.
Bayley et al., (1992). "Engineering 2,4-D resistance into cotton," Theor. Appl. Genet., 83:645-649.
Beachy et al., (1990). "Coat Protein-Mediated Resistance Against Virus Infection," Ann. Rev. Phytopathol., 28:451-474.
Clarke et al., (2006). "Embryo rescue and plant regeneration in vitro of selfed chickpea (*Cicer arietinum* L.) and its wild annual relatives," Plant Cell Tiss Organ Cult, 85:197-204.
Crossa et al., (2017). "Genomic selection in plant breeding: methods, models and perspectives," Trends in Plant Sciences, 22(11):961-975.
Fisher et al., (1993). "Starch branching enzyme II from maize endosperm," Plant Physiol., 102:1045-1046.
Fox et al., (1993). "Stearoyl-acyl carrier protein delta 9 desaturase from Ricinus communis is a diiron-oxo protein," PNAS USA, 90(6):2486-2490.
Foyer et al., (1995). "Overexpression of Glutathione Reductase but Not Glutathione Synthetase Leads to Increases in Antioxidant Capacity and Resistance to Photoinhibition in Poplar Trees," Plant Physiol., 109:1047-1057.
Gaur et al., (2016). "Inheritance of protein content and its relationships with seed size, grain yield and other traits in chickpea," Euphytica, 209:253-260, 8 pages.
Hayes et al., (1992). "Molecular cloning and heterologous expression of a cDNA encoding a mouse glutathione S-transferase Yc subunit possessing high catalytic activity for aflatoxin B1-8,9-epoxide," Biochem. J., 285:173-180, 8 pages.
Hayes, (2020). "Measuring protein content in food: an overview of methods," Foods, 9:1340, 4 pages.

(Continued)

*Primary Examiner* — Wayne Zhong
(74) *Attorney, Agent, or Firm* — Morrison & Foerster LLP

(57) ABSTRACT

New chickpea varieties designated 'NC-001'. 'NC-002', and 'NC-004' are chickpea varieties exhibiting stability and uniformity.

17 Claims, 17 Drawing Sheets
(17 of 17 Drawing Sheet(s) Filed in Color)

(56)　　　　　References Cited

OTHER PUBLICATIONS

Jones et al., (1994). "Isolation of the tomato Cf-9 gene for resistance to Cladosporium fulvum by transposon tagging," Science, 266:789-793.

Jukanti et al., (2012). "Nutritional quality and health benefits of chickpea (Cicer arietinum L.): a review," British Journal of Nutrition, 108:S11-S26.

Kharkwal, (1998). "Induced Mutations for Improvement of Protein in Chickpea (Cicer Arietinum L.)," Indian J Genet, 58(1):61-68.

Knutzon et al., (1992). "Modification of Brassica seed oil by antisense expression of a stearoyl-acyl carrier protein desaturase gene," PNAS USA, 89:2624-2628.

Lee et al., (1988). "The molecular basis of sulfonylurea herbicide resistance in tobacco," Embo J., 7(5):1241-1248.

Martin et al., (1993). "Map-based cloning of a protein kinase gene conferring disease resistance in tomato," Science, 262:1432-1436.

McCarthy, (2017). "The Rise of the Gluten-Free Diet", available online at <https://www.statista.com/chart/7639/the-rise-of-the-gluten-free-diet/>, 2 pages.

McDonough et al., (1992). "Specificity of unsaturated fatty acid-regulated expression of the Saccharomyces cerevisiae OLE1 gene," J. Biol. Chem., 267(9):5931-5936.

Mindrinos et al., (1994). "The A. thaliana disease resistance gene RPS2 encodes a protein containing a nucleotide-binding site and leucine-rich repeats," Cell, 78(6):1089-1099.

Patzoldt et al., (2006). "A codon deletion confers resistance to herbicides inhibiting protoporphyrinogen oxidase," PNAS, 103(33):12329-12334.

Przibilla et al., (1991). "Site-specific mutagenesis of the D1 subunit of photosystem II in wild-type Chlamydomonas," Plant Cell, 3:169-174.

Rao et al., (1989). "A tissue culture derived pesticide tolerant line of chickpea (Cicer arietinum L.)," Proc. Indian Acad. Sci. (Plant Sci.), 99:523-527.

Riazuddin et al., (1988). "Establishment of callus-tissue culture and the induction of organogenesis in chickpea," Pakistan Journal of Agricultural Research, 9(3):339-345.

Ryals et al., (1996). "Systemic Acquired Resistance," Plant Cell, 8:1809-1819.

Shiroza et al., (1988). "Sequence analysis of the Streptococcus mutans fructosyltransferase gene and flanking regions," J. Bacteriol., 170:810-816.

Singh et al., (1980), "Evaluation of Rapid Methods for the Estimation of Protein in Chickpea (Cicer arietinum L.)," J Sci Food Agric, 31:247-254.

Singh et al., (1983), "The protein content of chickpea (Cicer arietinum L.) grown at different locations," Qual Plant Plant Foods Hum Nutr, 32:179-194.

Singh et al., (1985), "Nutritional quality of chickpea (Cicer arietinum L.): current status and future research needs," Qual Plant Plant Foods Hum Nutr, 35:339-351.

Søgaard et al., (1993). "Site-directed Mutagenesis of Histidine 93, Aspartic Acid 180, Glutamic Acid 205, Histidine 290, and Aspartic Acid 291 at the Active Site and Tryptophan 279 at the Raw Starch Binding Site in Barley alpha-Amylase 1," J. Biol. Chem., 268(30):22480-22484.

Steinmetz et al., (1985). "The DNA Sequence of the Gene for the Secreted Bacillus subtilis Enzyme Levansucrase and Its Genetic Control Sites," Mol. Gen. Genet., 200:220-228.

Sumitani et al., (1993). "Molecular Cloning and Expression of Proteinaceous α-Amylase Inhibitor Gene from Streptomyces nitrosporeus in Escherichia coli," Biosci. Biotech. Biochem., 57(8):1243-1248.

Tang et al., (2017). "Food allergy: is prevalence increasing?" Intern Med J., 47(3):256-261.

Thomma et al., (2002). "Plant defensins," Planta, 216:193-202.

Watson et al., (2017). "Speed breeding: a powerful tool to accelerate crop research and breeding," Nature Plants, 4:23-29, 17 pages.

Arondel et al., (1992). "Map-based cloning of a gene controlling omega-3 fatty acid desaturation in Arabidopsis," Science, 258(5086):1353-1355.

De Greef et al., (1989). "Evaluation of Herbicide Resistance in Transgenic Crops Under Field Conditions," Biotechnology, 7:61-64.

Dutton, (1981). "History of the development of soy oil for edible uses," J Am Oil Chem Soc, 58:234-236.

Elliott et al., (1993). "Isolation and characterization of fruit vacuolar invertase genes from two tomato species and temporal differences in mRNA levels during fruit ripening," Plant Mol. Biol., 21:515-524.

Fang et al., (1992). "Sequence of two acetohydroxyacid synthase genes from Zea mays," Plant Mol. Biology, 18:1185-1187.

Geiser et al., (1986). "The hypervariable region in the genes coding for entomopathogenic crystal proteins of Bacillus thuringiensis: nucleotide sequence of the kurhd1 gene of subsp. kurstaki HD1," Gene, 48(1):109-118.

Kartha et al., (1981). "Plant regeneration from meristems of grain legumes: soybean, cowpea, peanut, chickpea, and bean," Canadian Journal of Botany, 59(9):1671-1679.

Linthorst et al., (1993). "Tobacco proteinase inhibitor I genes are locally, but not systemically induced by stress," Plant Mol Biol., 21:985-992.

Logemann et al., (1992). "Expression of a Barley Ribosome-Inactivating Protein Leads to Increased Fungal Protection in Transgenic Tobacco Plants," Biotechnology, 10:305-308, 4 pages.

Lou et al., (2010). "Improved extraction of oil from chickpea under ultrasound in a dynamic system," Journal of Food Engineering, 98:13-18.

Marshall et al., (1992). "Allelic mutations in acetyl-coenzyme A carboxylase confer herbicide tolerance in maize," Theor. Appl. Genet., 83:435-442.

Miki et al., (1990). "Transformation of Brassica napus canola cultivars with Arabidopsis thaliana acetohydroxyacid synthase genes and analysis of herbicide resistance," Theor. Appl. Genet., 80:449-458.

Pen et al., (1992). "Production of Active Bacillus licheniformis Alpha-Amylase in Tobacco and its Application in Starch Liquefaction," Bio/Technology, 10:292-296.

Peñaloza-Vázquez et al., (1995). "Expression of the hygromycin B phosphotransferase gene confers tolerance to the herbicide glyphosate," Plant Cell Reports, 14:482-487.

Reddy et al., (1993). "Isolation of a delta 6-desaturase gene from the cyanobacterium Synechocystis sp. strain PCC 6803 by gain-of-function expression in Anabaena sp. strain PCC 7120," Plant Mol. Biol., 27(2):293-300.

Sharma et al., (2013). "Nutritional and antinutritional profile of newly developed chickpea (Cicer arietinum L) varieties," International Food Research Journal, 20(2):805-810.

Van Damme et al., (1994). "Molecular cloning of mannose-binding lectins from Clivia miniata," Plant Mol Biol., 24(5):825-830.

Wan et al., (1989). "Efficient production of doubled haploid plants through colchicine treatment of anther-derived maize callus," Theor. Appl. Genet., 77:889-892.

* cited by examiner

CHICKPEA VARIETY 'NC-001'

CROSS-REFERENCE TO RELATED APPLICATION

This application claims the benefit of U.S. Provisional Application No. 63/411,236, filed Sep. 29, 2022, which is hereby incorporated by reference in its entirety.

FIELD OF THE INVENTION

The present invention relates to the field of plant breeding. In particular, this invention relates to new chickpea, composed of wild germplasm (*Cicer reticulatum* or *Cicer echniospermum*) introgressed into cultivated chickpea (*Cicer arietinum* L.), varieties designated 'NC-001', 'NC-002', 'NC-003', 'NC-004', 'NC-005', 'NC-006', 'NC-007', 'NC-008', and 'NC-009'.

BACKGROUND OF THE INVENTION

Concerns about the impact of agriculture on the environment and changing consumer preferences have led to an increased demand for alternative sources of plant-based protein and gluten-free flour. For example, in recent years, there has been a notable increase in the number of consumers who choose to eat vegetarian or vegan diets for a variety of reasons, including animal welfare, environmental concern and religious beliefs. This has led to a need for affordable, nutritious, and scalable plant-based protein sources that can serve as ingredients for animal-alternative products, such as plant-based meat-, dairy-, and egg-like products, as well as sports protein products, snack foods, baby foods, pastas, baked goods, and other food and beverage products. In another example, the number of consumers who eat gluten-free has also risen dramatically (McCarthy. 2017. "The Rise of the Gluten-Free Diet", Statistica, www[dot]statista[dot]com/chart/7639/the-rise-of-the-gluten-free-diet/), leading to demand for additional variety and nutrition content in gluten-free products. Further, with an increased prevalence of food allergies experienced in recent years and expected to continue in the coming years, (Tang and Mullins. 2017. Food allergy: is prevalence increasing? *Intern Med J*. 47(3): 256-261), it is beneficial for food and beverage products to avoid common food allergens such as tree nuts, peanuts, wheat, and soy. All of these factors converge to create a need for new sources of plant-based protein ingredients and gluten free flours.

Chickpeas (*Cicer arietinum* L., also known as garbanzo beans) are a major grain legume crop valued in cuisines worldwide, the production of which is surpassed only by the common bean (*Phaseolus vulgaris* L.). Chickpeas, which refers to the seeds of the *Cicer arietinum* L. plant, may be cooked and eaten whole in stews, salads, and other dishes or processed into pastes or batter. Alternatively, chickpeas can be dried and ground into flour for use in cooking and baking. Chickpeas are free of gluten and common food allergens, and are of interest as a source of protein isolates and concentrates for the production of plant-based foods. *Cicer arietinum* L. originated in the Near East and consists of two major cultivar groups: 1) the desi group, with smaller and darker-colored grains, grown mainly east of the Near East; and 2) the kabuli group, with larger and lighter colored grains, grown in the Mediterranean and the Americas. In the United States, kabuli varieties are the most commonly eaten and produced, with the most popular varieties exhibiting the largest seed size and light-beige grains. By contrast, wild or uncultivated species of *Cicer arietinum* L., as well as wild relatives of *Cicer arietinum* L. (e.g., *Cicer reticulatum*), exhibit a wide variety of grain colors, shapes, and nutritional contents. While extensive genetic diversity exists in these wild varieties, the vast majority of this diversity was lost in the process of chickpea domestication, limiting the potential phenotypic potential of the most commonly-cultivated varieties.

Accordingly, there is a continuing need to develop chickpea varieties with greater genetic diversity as a source of plant-based protein and gluten-free flour.

SUMMARY OF THE INVENTION

In order to meet these needs, the present invention is directed to improved chickpea varieties.

As used herein, chickpea variety 'NC-001' is the same chickpea variety as chickpea variety 'N_22_001' having ATCC Accession Number X1 and disclosed in U.S. Provisional Application No. 63/411,236. While the name has changed, chickpea variety 'NC-001' has all the defining characteristics of chickpea variety 'N_22_001'. As used herein, chickpea variety 'NC-002' is the same chickpea variety as chickpea variety 'N_22_002' having ATCC Accession Number X2 and disclosed in U.S. Provisional Application No. 63/411,236. While the name has changed, chickpea variety 'NC-002' has all the defining characteristics of chickpea variety 'N_22_002'. As used herein, chickpea variety 'NC-003' is the same chickpea variety as chickpea variety 'N_22_003' having ATCC Accession Number X3 and disclosed in U.S. Provisional Application No. 63/411,236. While the name has changed, chickpea variety 'NC-003' has all the defining characteristics of chickpea variety 'N_22_003'. As used herein, chickpea variety 'NC-004' is the same chickpea variety as chickpea variety 'N_22_004' having ATCC Accession Number X4 and disclosed in U.S. Provisional Application No. 63/411,236. While the name has changed, chickpea variety 'NC-004' has all the defining characteristics of chickpea variety 'N_22_004'. As used herein, chickpea variety 'NC-005' is the same chickpea variety as chickpea variety 'N_22_005' having ATCC Accession Number X5 and disclosed in U.S. Provisional Application No. 63/411,236. While the name has changed, chickpea variety 'NC-005' has all the defining characteristics of chickpea variety 'N_22_005'. As used herein, chickpea variety 'NC-006' is the same chickpea variety as chickpea variety 'N_22_006' having ATCC Accession Number X6 and disclosed in U.S. Provisional Application No. 63/411,236. While the name has changed, chickpea variety 'NC-006' has all the defining characteristics of chickpea variety 'N_22_006'. As used herein, chickpea variety 'NC-007' is the same chickpea variety as chickpea variety 'N_22_007' having ATCC Accession Number X7 and disclosed in U.S. Provisional Application No. 63/411,236. While the name has changed, chickpea variety 'NC-007' has all the defining characteristics of chickpea variety 'N_22_007'. As used herein, chickpea variety 'NC-008' is the same chickpea variety as chickpea variety 'N_22_008' having ATCC Accession Number X8 and disclosed in U.S. Provisional Application No. 63/411,236. While the name has changed, chickpea variety 'NC-008' has all the defining characteristics of chickpea variety 'N_22_008'. As used herein, chickpea variety 'NC-009' is the same chickpea variety as chickpea variety 'N_22_009' having ATCC Accession Number X9 and disclosed in U.S. Provisional Application No. 63/411,236. While the name has changed, chickpea variety 'NC-009' has all the defining characteristics of chickpea variety 'N_22_009'.

In one aspect, the present invention is directed to chickpea seed designated as 'NC-001' having ATCC Accession Number PTA-127935. In one embodiment, the present invention is directed to a chickpea plant and parts isolated therefrom produced by growing 'NC-001' chickpea seed. In another embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from 'NC-001' chickpea plants. In a certain embodiment, the present invention is further directed to a chickpea seed isolated from 'NC-001' chickpea plants.

In another aspect, the present invention is directed to a chickpea plant and parts isolated therefrom having all the physiological and morphological characteristics of a chickpea plant produced by growing 'NC-001' chickpea seed having ATCC Accession Number PTA-127935. In one embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from a chickpea plant having all the physiological and morphological characteristics of a chickpea plant produced by growing 'NC-001' chickpea seed. In a certain embodiment, the present invention is further directed to a chickpea seed isolated from a chickpea plant having all the physiological and morphological characteristics of a chickpea plant produced by growing 'NC-001' chickpea seed.

In another aspect, the present invention is further directed to tissue culture or cells derived from 'NC-001' chickpea plants. In one embodiment, the present invention provides a tissue culture of protoplasts or regenerable cells from a plant or parts thereof, produced by growing seed designated 'NC-001'. In another embodiment, the present invention provides a chickpea plant regenerated from tissue culture, wherein the plant has all of the morphological and physiological characteristics of a chickpea plant produced by growing seed designated as 'NC-001' having ATCC Accession Number PTA-127935.

In still another aspect, the present invention is directed to an $F_1$ hybrid chickpea seed, a plant grown from the seed, or a plant part isolated therefrom having 'NC-001' as a parent, wherein 'NC-001' is grown from 'NC-001' chickpea seed having ATCC Accession Number PTA-127935. In another embodiment, the present invention is directed to a pollen grain, an ovule, a protoplast, a cell, an embryo, a cotyledon, a hypocotyl, a meristem, a root, a pistil, an anther, a flower, a stem, a pod, a leaf, a petiole, or a portion thereof isolated from an $F_1$ hybrid chickpea plant, having 'NC-001' as a parent, wherein 'NC-001' is grown from 'NC-001' chickpea seed having ATCC Accession Number PTA-127935.

In another aspect, the present invention is directed to a method of making chickpea seeds, said method comprising crossing the chickpea plant produced by growing 'NC-001' chickpea seed with another chickpea plant and harvesting seed therefrom.

In a further aspect, the present invention is directed to a method of making the chickpea variety 'NC-001', said method comprising selecting seeds from the cross of one 'NC-001' plant with another 'NC-001' plant, a sample of 'NC-001' chickpea seed having been deposited under ATCC Accession Number PTA-127935.

In another aspect, the present invention is directed to a method of producing a seed of a 'NC-001'-derived chickpea plant, comprising the steps of a) crossing a chickpea variety designated as 'NC-001' having ATCC Accession Number PTA-127935, with itself or a second chickpea plant; and b) allowing seed of a 'NC-001'-derived chickpea plant to form. In one embodiment, the method of producing a seed of a 'NC-001'-derived chickpea plant further comprises the steps of c) crossing a plant grown from 'NC-001'-derived chickpea seed with itself or a second chickpea plant to yield additional 'NC-001'-derived chickpea seed; d) growing the additional 'NC-001'-derived chickpea seed of step (c) to yield additional 'NC-001'-derived chickpea plants; and e) repeating steps (c) and (d) for an additional 3-10 generations to generate further 'NC-001'-derived chickpea plants.

In another aspect, the present invention is directed to methods of producing a chickpea plant having one or more value-added traits by introducing one or more genes conferring one or more value-added traits into a chickpea plant produced by growing 'NC-001' chickpea seed having ATCC Accession Number PTA-127935. Some embodiments are directed to chickpea plants having one or more value-added trait produced by such methods. In one embodiment, the present invention provides methods of producing an herbicide resistant chickpea plant by introducing a gene conferring herbicide resistance into a chickpea plant produced by growing 'NC-001' chickpea seed, and to herbicide resistant chickpea plants produced by such methods. In another embodiment, the present invention provides methods of producing a pest or insect resistant chickpea plant by introducing a gene conferring pest or insect resistance into a chickpea plant produced by growing 'NC-001' chickpea seed, and to pest or insect resistant chickpea plants produced by such methods. In yet another embodiment, the present invention provides methods of producing a disease resistant chickpea plant by introducing a gene conferring disease resistance into a chickpea plant produced by growing 'NC-001' chickpea seed, and to disease resistant chickpea plants produced by such methods.

In yet another aspect, the present invention provides a method of producing a commodity plant product, comprising obtaining the chickpea plant produced by growing 'NC-001' chickpea seed having ATCC Accession Number PTA-127935, or a plant part thereof, and producing said commodity plant product therefrom. In one embodiment, the plant part is a seed. In one embodiment, the commodity plant product is a protein isolate, a protein concentrate, a texturized protein product, a meal, a flour, a starch, a fiber, or an oil. In one embodiment, the present invention is further directed to packaging material containing 'NC-001' plant parts or a commodity plant product produced therefrom. The 'NC-001' plant parts, or commodity plant products produced therefrom, may be combined with other plant parts of other plant varieties, other commodity plant products, food products, food ingredients, and the like.

In one aspect, the present invention is directed to chickpea seed designated as 'NC-002' having ATCC Accession Number X2. In one embodiment, the present invention is directed to a chickpea plant and parts isolated therefrom produced by growing 'NC-002' chickpea seed. In another embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from 'NC-002' chickpea plants. In a certain embodiment, the present invention is further directed to a chickpea seed isolated from 'NC-002' chickpea plants.

In another aspect, the present invention is directed to a chickpea plant and parts isolated therefrom having all the physiological and morphological characteristics of a chickpea plant produced by growing 'NC-002' chickpea seed having ATCC Accession Number X2. In one embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from a chickpea plant having all the physiological and morphological characteristics of a chickpea plant produced by growing 'NC-002' chickpea seed. In a certain embodiment, the present invention is further directed to a chickpea seed isolated from a chickpea plant having all the physiological and morphological characteristics of a chickpea plant produced by growing 'NC-002' chickpea seed.

In another aspect, the present invention is further directed to tissue culture or cells derived from 'NC-002' chickpea plants. In one embodiment, the present invention provides a tissue culture of protoplasts or regenerable cells from a plant or parts thereof, produced by growing seed designated 'NC-002'. In another embodiment, the present invention provides a chickpea plant regenerated from tissue culture, wherein the plant has all of the morphological and physiological characteristics of a chickpea plant produced by growing seed designated as 'NC-002' having ATCC Accession Number X2.

In still another aspect, the present invention is directed to an $F_1$ hybrid chickpea seed, a plant grown from the seed, or a plant part isolated therefrom having 'NC-002' as a parent, wherein 'NC-002' is grown from 'NC-002' chickpea seed having ATCC Accession Number X2. In another embodiment, the present invention is directed to a pollen grain, an ovule, a protoplast, a cell, an embryo, a cotyledon, a hypocotyl, a meristem, a root, a pistil, an anther, a flower, a stem, a pod, a leaf, a petiole, or a portion thereof isolated from an $F_1$ hybrid chickpea plant, having 'NC-002' as a parent, wherein 'NC-002' is grown from 'NC-002' chickpea seed having ATCC Accession Number X2.

In another aspect, the present invention is directed to a method of making chickpea seeds, said method comprising crossing the chickpea plant produced by growing 'NC-002' chickpea seed with another chickpea plant and harvesting seed therefrom.

In a further aspect, the present invention is directed to a method of making the chickpea variety 'NC-002', said method comprising selecting seeds from the cross of one 'NC-002' plant with another 'NC-002' plant, a sample of 'NC-002' chickpea seed having been deposited under ATCC Accession Number X2.

In another aspect, the present invention is directed to a method of producing a seed of a 'NC-002'-derived chickpea plant, comprising the steps of a) crossing a chickpea variety designated as 'NC-002' having ATCC Accession Number X2, with itself or a second chickpea plant; and b) allowing seed of a 'NC-002'-derived chickpea plant to form. In one embodiment, the method of producing a seed of a 'NC-002'-derived chickpea plant further comprises the steps of c) crossing a plant grown from 'NC-002'-derived chickpea seed with itself or a second chickpea plant to yield additional 'NC-002'-derived chickpea seed; d) growing the additional 'NC-002'-derived chickpea seed of step (c) to yield additional 'NC-002'-derived chickpea plants; and e) repeating steps (c) and (d) for an additional 3-10 generations to generate further 'NC-002'-derived chickpea plants.

In another aspect, the present invention is directed to methods of producing a chickpea plant having one or more value-added traits by introducing one or more genes conferring one or more value-added traits into a chickpea plant produced by growing 'NC-002' chickpea seed having ATCC Accession Number X2. Some embodiments are directed to chickpea plants having one or more value-added trait produced by such methods. In one embodiment, the present invention provides methods of producing an herbicide resistant chickpea plant by introducing a gene conferring herbicide resistance into a chickpea plant produced by growing 'NC-002' chickpea seed, and to herbicide resistant chickpea plants produced by such methods. In another embodiment, the present invention provides methods of producing a pest or insect resistant chickpea plant by introducing a gene conferring pest or insect resistance into a chickpea plant produced by growing 'NC-002' chickpea seed, and to pest or insect resistant chickpea plants produced by such methods. In yet another embodiment, the present invention provides methods of producing a disease resistant chickpea plant by introducing a gene conferring disease resistance into a chickpea plant produced by growing 'NC-002' chickpea seed, and to disease resistant chickpea plants produced by such methods.

In yet another aspect, the present invention provides a method of producing a commodity plant product, comprising obtaining the chickpea plant produced by growing 'NC-002' chickpea seed having ATCC Accession Number X2, or a plant part thereof, and producing said commodity plant product therefrom. In one embodiment, the plant part is a seed. In one embodiment, the commodity plant product is a protein isolate, a protein concentrate, a texturized protein product, a meal, a flour, a starch, a fiber, or an oil. In one embodiment, the present invention is further directed to packaging material containing 'NC-002' plant parts or a commodity plant product produced therefrom. The 'NC-002' plant parts, or commodity plant products produced therefrom, may be combined with other plant parts of other plant varieties, other commodity plant products, food products, food ingredients, and the like.

In one aspect, the present invention is directed to chickpea seed designated as 'NC-003' having ATCC Accession Number X3. In one embodiment, the present invention is directed to a chickpea plant and parts isolated therefrom produced by growing 'NC-003' chickpea seed. In another embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from 'NC-003' chickpea plants. In a certain embodiment, the present invention is further directed to a chickpea seed isolated from 'NC-003' chickpea plants.

In another aspect, the present invention is directed to a chickpea plant and parts isolated therefrom having all the physiological and morphological characteristics of a chickpea plant produced by growing 'NC-003' chickpea seed having ATCC Accession Number X3. In one embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from a chickpea plant having all the physiological and morphological characteristics of a chickpea plant produced by growing 'NC-003' chickpea seed. In a certain embodiment, the present invention is further directed to a chickpea seed isolated from a chickpea plant having all the physiological and morphological characteristics of a chickpea plant produced by growing 'NC-003' chickpea seed.

In another aspect, the present invention is further directed to tissue culture or cells derived from 'NC-003' chickpea plants. In one embodiment, the present invention provides a tissue culture of protoplasts or regenerable cells from a plant or parts thereof, produced by growing seed designated 'NC-003'. In another embodiment, the present invention provides a chickpea plant regenerated from tissue culture, wherein the plant has all of the morphological and physiological characteristics of a chickpea plant produced by growing seed designated as 'NC-003' having ATCC Accession Number X3.

In still another aspect, the present invention is directed to an $F_1$ hybrid chickpea seed, a plant grown from the seed, or a plant part isolated therefrom having 'NC-003' as a parent, wherein 'NC-003' is grown from 'NC-003' chickpea seed having ATCC Accession Number X3. In another embodiment, the present invention is directed to a pollen grain, an ovule, a protoplast, a cell, an embryo, a cotyledon, a hypocotyl, a meristem, a root, a pistil, an anther, a flower, a stem, a pod, a leaf, a petiole, or a portion thereof isolated from an $F_1$ hybrid chickpea plant, having 'NC-003' as a parent, wherein 'NC-003' is grown from 'NC-003' chickpea seed having ATCC Accession Number X3.

In another aspect, the present invention is directed to a method of making chickpea seeds, said method comprising crossing the chickpea plant produced by growing 'NC-003' chickpea seed with another chickpea plant and harvesting seed therefrom.

In a further aspect, the present invention is directed to a method of making the chickpea variety 'NC-003', said method comprising selecting seeds from the cross of one 'NC-003' plant with another 'NC-003' plant, a sample of 'NC-003' chickpea seed having been deposited under ATCC Accession Number X3.

In another aspect, the present invention is directed to a method of producing a seed of a 'NC-003'-derived chickpea plant, comprising the steps of a) crossing a chickpea variety designated as 'NC-003' having ATCC Accession Number X3, with itself or a second chickpea plant; and b) allowing seed of a 'NC-003'-derived chickpea plant to form. In one embodiment, the method of producing a seed of a 'NC-003'-derived chickpea plant further comprises the steps of c) crossing a plant grown from 'NC-003'-derived chickpea seed with itself or a second chickpea plant to yield additional 'NC-003'-derived chickpea seed; d) growing the additional 'NC-003'-derived chickpea seed of step (c) to yield additional 'NC-003'-derived chickpea plants; and e) repeating steps (c) and (d) for an additional 3-10 generations to generate further 'NC-003'-derived chickpea plants.

In another aspect, the present invention is directed to methods of producing a chickpea plant having one or more value-added traits by introducing one or more genes conferring one or more value-added traits into a chickpea plant produced by growing 'NC-003' chickpea seed having ATCC Accession Number X3. Some embodiments are directed to chickpea plants having one or more value-added trait produced by such methods. In one embodiment, the present invention provides methods of producing an herbicide resistant chickpea plant by introducing a gene conferring herbicide resistance into a chickpea plant produced by growing 'NC-003' chickpea seed, and to herbicide resistant chickpea plants produced by such methods. In another embodiment, the present invention provides methods of producing a pest or insect resistant chickpea plant by introducing a gene conferring pest or insect resistance into a chickpea plant produced by growing 'NC-003' chickpea seed, and to pest or insect resistant chickpea plants produced by such methods. In yet another embodiment, the present invention provides methods of producing a disease resistant chickpea plant by introducing a gene conferring disease resistance into a chickpea plant produced by growing 'NC-003' chickpea seed, and to disease resistant chickpea plants produced by such methods.

In yet another aspect, the present invention provides a method of producing a commodity plant product, comprising obtaining the chickpea plant produced by growing 'NC-003' chickpea seed having ATCC Accession Number X3, or a plant part thereof, and producing said commodity plant product therefrom. In one embodiment, the plant part is a seed. In one embodiment, the commodity plant product is a protein isolate, a protein concentrate, a texturized protein product, a meal, a flour, a starch, a fiber, or an oil. In one embodiment, the present invention is further directed to packaging material containing 'NC-003' plant parts or a commodity plant product produced therefrom. The 'NC-003' plant parts, or commodity plant products produced therefrom, may be combined with other plant parts of other plant varieties, other commodity plant products, food products, food ingredients, and the like.

In one aspect, the present invention is directed to chickpea seed designated as 'NC-004' having ATCC Accession Number X4. In one embodiment, the present invention is directed to a chickpea plant and parts isolated therefrom produced by growing 'NC-004' chickpea seed. In another embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from 'NC-004' chickpea plants. In a certain embodiment, the present invention is further directed to a chickpea seed isolated from 'NC-004' chickpea plants.

In another aspect, the present invention is directed to a chickpea plant and parts isolated therefrom having all the physiological and morphological characteristics of a chickpea plant produced by growing 'NC-004' chickpea seed having ATCC Accession Number X4. In one embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from a chickpea plant having all the physiological and morphological characteristics of a chickpea plant produced by growing 'NC-004' chickpea seed. In a certain embodiment, the present invention is further directed to a chickpea seed isolated from a chickpea plant having all the physiological and morphological characteristics of a chickpea plant produced by growing 'NC-004' chickpea seed.

In another aspect, the present invention is further directed to tissue culture or cells derived from 'NC-004' chickpea plants. In one embodiment, the present invention provides a tissue culture of protoplasts or regenerable cells from a plant or parts thereof, produced by growing seed designated 'NC-004'. In another embodiment, the present invention provides a chickpea plant regenerated from tissue culture, wherein the plant has all of the morphological and physiological characteristics of a chickpea plant produced by growing seed designated as 'NC-004' having ATCC Accession Number X4.

In still another aspect, the present invention is directed to an $F_1$ hybrid chickpea seed, a plant grown from the seed, or a plant part isolated therefrom having 'NC-004' as a parent, wherein 'NC-004' is grown from 'NC-004' chickpea seed having ATCC Accession Number X4. In another embodiment, the present invention is directed to a pollen grain, an ovule, a protoplast, a cell, an embryo, a cotyledon, a hypocotyl, a meristem, a root, a pistil, an anther, a flower, a stem, a pod, a leaf, a petiole, or a portion thereof isolated from an $F_1$ hybrid chickpea plant, having 'NC-004' as a parent, wherein 'NC-004' is grown from 'NC-004' chickpea seed having ATCC Accession Number X4.

In another aspect, the present invention is directed to a method of making chickpea seeds, said method comprising crossing the chickpea plant produced by growing 'NC-004' chickpea seed with another chickpea plant and harvesting seed therefrom.

In a further aspect, the present invention is directed to a method of making the chickpea variety 'NC-004', said method comprising selecting seeds from the cross of one 'NC-004' plant with another 'NC-004' plant, a sample of 'NC-004' chickpea seed having been deposited under ATCC Accession Number X4.

In another aspect, the present invention is directed to a method of producing a seed of a 'NC-004'-derived chickpea plant, comprising the steps of a) crossing a chickpea variety designated as 'NC-004' having ATCC Accession Number X4, with itself or a second chickpea plant; and b) allowing seed of a 'NC-004'-derived chickpea plant to form. In one embodiment, the method of producing a seed of a 'NC-004'-derived chickpea plant further comprises the steps of c) crossing a plant grown from 'NC-004'-derived chickpea seed with itself or a second chickpea plant to yield additional 'NC-004'-derived chickpea seed; d) growing the additional 'NC-004'-derived chickpea seed of step (c) to yield additional 'NC-004'-derived chickpea plants; and e) repeating steps (c) and (d) for an additional 3-10 generations to generate further 'NC-004'-derived chickpea plants.

In another aspect, the present invention is directed to methods of producing a chickpea plant having one or more value-added traits by introducing one or more genes conferring one or more value-added traits into a chickpea plant produced by growing 'NC-004' chickpea seed having ATCC Accession Number X4. Some embodiments are directed to chickpea plants having one or more value-added trait produced by such methods. In one embodiment, the present invention provides methods of producing an herbicide resistant chickpea plant by introducing a gene conferring herbicide resistance into a chickpea plant produced by growing 'NC-004' chickpea seed, and to herbicide resistant chickpea plants produced by such methods. In another embodiment, the present invention provides methods of producing a pest or insect resistant chickpea plant by introducing a gene conferring pest or insect resistance into a chickpea plant produced by growing 'NC-004' chickpea seed, and to pest or insect resistant chickpea plants produced by such methods. In yet another embodiment, the present invention provides methods of producing a disease resistant chickpea plant by introducing a gene conferring disease resistance into a chickpea plant produced by growing 'NC-004' chickpea seed, and to disease resistant chickpea plants produced by such methods.

In yet another aspect, the present invention provides a method of producing a commodity plant product, comprising obtaining the chickpea plant produced by growing 'NC-004' chickpea seed having ATCC Accession Number X4, or a plant part thereof, and producing said commodity plant product therefrom. In one embodiment, the plant part is a seed. In one embodiment, the commodity plant product is a protein isolate, a protein concentrate, a texturized protein product, a meal, a flour, a starch, a fiber, or an oil. In one embodiment, the present invention is further directed to packaging material containing 'NC-004' plant parts or a commodity plant product produced therefrom. The 'NC-004' plant parts, or commodity plant products produced therefrom, may be combined with other plant parts of other plant varieties, other commodity plant products, food products, food ingredients, and the like.

In one aspect, the present invention is directed to chickpea seed designated as 'NC-005' having ATCC Accession Number X5. In one embodiment, the present invention is directed to a chickpea plant and parts isolated therefrom produced by growing 'NC-005' chickpea seed. In another embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from 'NC-005' chickpea plants. In a certain embodiment, the present invention is further directed to a chickpea seed isolated from 'NC-005' chickpea plants.

In another aspect, the present invention is directed to a chickpea plant and parts isolated therefrom having all the physiological and morphological characteristics of a chickpea plant produced by growing 'NC-005' chickpea seed having ATCC Accession Number X5. In one embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from a chickpea plant having all the physiological and morphological characteristics of a chickpea plant produced by growing 'NC-005' chickpea seed. In a certain embodiment, the present invention is further directed to a chickpea seed isolated from a chickpea plant having all the physiological and morphological characteristics of a chickpea plant produced by growing 'NC-005' chickpea seed.

In another aspect, the present invention is further directed to tissue culture or cells derived from 'NC-005' chickpea plants. In one embodiment, the present invention provides a tissue culture of protoplasts or regenerable cells from a plant or parts thereof, produced by growing seed designated 'NC-005'. In another embodiment, the present invention provides a chickpea plant regenerated from tissue culture, wherein the plant has all of the morphological and physiological characteristics of a chickpea plant produced by growing seed designated as 'NC-005' having ATCC Accession Number X5.

In still another aspect, the present invention is directed to an $F_1$ hybrid chickpea seed, a plant grown from the seed, or a plant part isolated therefrom having 'NC-005' as a parent, wherein 'NC-005' is grown from 'NC-005' chickpea seed having ATCC Accession Number X5. In another embodiment, the present invention is directed to a pollen grain, an ovule, a protoplast, a cell, an embryo, a cotyledon, a hypocotyl, a meristem, a root, a pistil, an anther, a flower, a stem, a pod, a leaf, a petiole, or a portion thereof isolated from an $F_1$ hybrid chickpea plant, having 'NC-005' as a parent, wherein 'NC-005' is grown from 'NC-005' chickpea seed having ATCC Accession Number X5.

In another aspect, the present invention is directed to a method of making chickpea seeds, said method comprising crossing the chickpea plant produced by growing 'NC-005' chickpea seed with another chickpea plant and harvesting seed therefrom.

In a further aspect, the present invention is directed to a method of making the chickpea variety 'NC-005', said method comprising selecting seeds from the cross of one 'NC-005' plant with another 'NC-005' plant, a sample of 'NC-005' chickpea seed having been deposited under ATCC Accession Number X5.

In another aspect, the present invention is directed to a method of producing a seed of a 'NC-005'-derived chickpea plant, comprising the steps of a) crossing a chickpea variety designated as 'NC-005' having ATCC Accession Number X5, with itself or a second chickpea plant; and b) allowing seed of a 'NC-005'-derived chickpea plant to form. In one embodiment, the method of producing a seed of a 'NC-005'-derived chickpea plant further comprises the steps of c) crossing a plant grown from 'NC-005'-derived chickpea seed with itself or a second chickpea plant to yield additional 'NC-005'-derived chickpea seed; d) growing the additional 'NC-005'-derived chickpea seed of step (c) to yield additional 'NC-005'-derived chickpea plants; and e) repeating steps (c) and (d) for an additional 3-10 generations to generate further 'NC-005'-derived chickpea plants.

In another aspect, the present invention is directed to methods of producing a chickpea plant having one or more value-added traits by introducing one or more genes conferring one or more value-added traits into a chickpea plant produced by growing 'NC-005' chickpea seed having ATCC Accession Number X5. Some embodiments are directed to chickpea plants having one or more value-added trait produced by such methods. In one embodiment, the present invention provides methods of producing an herbicide resistant chickpea plant by introducing a gene conferring herbicide resistance into a chickpea plant produced by growing 'NC-005' chickpea seed, and to herbicide resistant chickpea plants produced by such methods. In another embodiment, the present invention provides methods of producing a pest or insect resistant chickpea plant by introducing a gene conferring pest or insect resistance into a chickpea plant produced by growing 'NC-005' chickpea seed, and to pest or insect resistant chickpea plants produced by such methods. In yet another embodiment, the present invention provides methods of producing a disease resistant chickpea plant by introducing a gene conferring disease resistance into a chickpea plant produced by growing 'NC-005' chickpea seed, and to disease resistant chickpea plants produced by such methods.

In yet another aspect, the present invention provides a method of producing a commodity plant product, comprising obtaining the chickpea plant produced by growing 'NC-005' chickpea seed having ATCC Accession Number X5, or a plant part thereof, and producing said commodity plant product therefrom. In one embodiment, the plant part is a seed. In one embodiment, the commodity plant product is a protein isolate, a protein concentrate, a texturized protein product, a meal, a flour, a starch, a fiber, or an oil. In one embodiment, the present invention is further directed to packaging material containing 'NC-005' plant parts or a commodity plant product produced therefrom. The 'NC-005' plant parts, or commodity plant products produced therefrom, may be combined with other plant parts of other plant varieties, other commodity plant products, food products, food ingredients, and the like.

In one aspect, the present invention is directed to chickpea seed designated as 'NC-006' having ATCC Accession Number X6. In one embodiment, the present invention is directed to a chickpea plant and parts isolated therefrom produced by growing 'NC-006' chickpea seed. In another embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from 'NC-006' chickpea plants. In a certain embodiment, the present invention is further directed to a chickpea seed isolated from 'NC-006' chickpea plants.

In another aspect, the present invention is directed to a chickpea plant and parts isolated therefrom having all the physiological and morphological characteristics of a chickpea plant produced by growing 'NC-006' chickpea seed having ATCC Accession Number X6. In one embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from a chickpea plant having all the physiological and morphological characteristics of a chickpea plant produced by growing 'NC-006' chickpea seed. In a certain embodiment, the present invention is further directed to a chickpea seed isolated from a chickpea plant having all the physiological and morphological characteristics of a chickpea plant produced by growing 'NC-006' chickpea seed.

In another aspect, the present invention is further directed to tissue culture or cells derived from 'NC-006' chickpea plants. In one embodiment, the present invention provides a tissue culture of protoplasts or regenerable cells from a plant or parts thereof, produced by growing seed designated 'NC-006'. In another embodiment, the present invention provides a chickpea plant regenerated from tissue culture, wherein the plant has all of the morphological and physiological characteristics of a chickpea plant produced by growing seed designated as 'NC-006' having ATCC Accession Number X6.

In still another aspect, the present invention is directed to an $F_1$ hybrid chickpea seed, a plant grown from the seed, or a plant part isolated therefrom having 'NC-006' as a parent, wherein 'NC-006' is grown from 'NC-006' chickpea seed having ATCC Accession Number X6. In another embodiment, the present invention is directed to a pollen grain, an ovule, a protoplast, a cell, an embryo, a cotyledon, a hypocotyl, a meristem, a root, a pistil, an anther, a flower, a stem, a pod, a leaf, a petiole, or a portion thereof isolated from an $F_1$ hybrid chickpea plant, having 'NC-006' as a parent, wherein 'NC-006' is grown from 'NC-006' chickpea seed having ATCC Accession Number X6.

In another aspect, the present invention is directed to a method of making chickpea seeds, said method comprising crossing the chickpea plant produced by growing 'NC-006' chickpea seed with another chickpea plant and harvesting seed therefrom.

In a further aspect, the present invention is directed to a method of making the chickpea variety 'NC-006', said method comprising selecting seeds from the cross of one 'NC-006' plant with another 'NC-006' plant, a sample of 'NC-006' chickpea seed having been deposited under ATCC Accession Number X6.

In another aspect, the present invention is directed to a method of producing a seed of a 'NC-006'-derived chickpea plant, comprising the steps of a) crossing a chickpea variety designated as 'NC-006' having ATCC Accession Number X6, with itself or a second chickpea plant; and b) allowing seed of a 'NC-006'-derived chickpea plant to form. In one embodiment, the method of producing a seed of a 'NC-006'-derived chickpea plant further comprises the steps of c) crossing a plant grown from 'NC-006'-derived chickpea seed with itself or a second chickpea plant to yield additional 'NC-006'-derived chickpea seed; d) growing the additional 'NC-006'-derived chickpea seed of step (c) to yield additional 'NC-006'-derived chickpea plants; and e) repeating steps (c) and (d) for an additional 3-10 generations to generate further 'NC-006'-derived chickpea plants.

In another aspect, the present invention is directed to methods of producing a chickpea plant having one or more value-added traits by introducing one or more genes conferring one or more value-added traits into a chickpea plant produced by growing 'NC-006' chickpea seed having ATCC Accession Number X6. Some embodiments are directed to chickpea plants having one or more value-added trait produced by such methods. In one embodiment, the present invention provides methods of producing an herbicide resistant chickpea plant by introducing a gene conferring herbicide resistance into a chickpea plant produced by growing 'NC-006' chickpea seed, and to herbicide resistant chickpea plants produced by such methods. In another embodiment, the present invention provides methods of producing a pest or insect resistant chickpea plant by introducing a gene conferring pest or insect resistance into a chickpea plant produced by growing 'NC-006' chickpea seed, and to pest or insect resistant chickpea plants produced by such methods. In yet another embodiment, the present invention provides methods of producing a disease resistant chickpea plant by introducing a gene conferring disease resistance into a chickpea plant produced by growing 'NC-006' chickpea seed, and to disease resistant chickpea plants produced by such methods.

In yet another aspect, the present invention provides a method of producing a commodity plant product, comprising obtaining the chickpea plant produced by growing 'NC-006' chickpea seed having ATCC Accession Number X6, or a plant part thereof, and producing said commodity plant product therefrom. In one embodiment, the plant part is a seed. In one embodiment, the commodity plant product is a protein isolate, a protein concentrate, a texturized protein product, a meal, a flour, a starch, a fiber, or an oil. In one embodiment, the present invention is further directed to packaging material containing 'NC-006' plant parts or a commodity plant product produced therefrom. The 'NC-006' plant parts, or commodity plant products produced therefrom, may be combined with other plant parts of other plant varieties, other commodity plant products, food products, food ingredients, and the like.

In one aspect, the present invention is directed to chickpea seed designated as 'NC-007' having ATCC Accession Number X7. In one embodiment, the present invention is directed to a chickpea plant and parts isolated therefrom produced by growing 'NC-007' chickpea seed. In another embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from 'NC-007' chickpea plants. In a certain embodiment, the present invention is further directed to a chickpea seed isolated from 'NC-007' chickpea plants.

In another aspect, the present invention is directed to a chickpea plant and parts isolated therefrom having all the physiological and morphological characteristics of a chickpea plant produced by growing 'NC-007' chickpea seed having ATCC Accession Number X7. In one embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from a chickpea plant having all the physiological and morphological characteristics of a chickpea plant produced by growing 'NC-007' chickpea seed. In a certain embodiment, the present invention is further directed to a chickpea seed isolated from a chickpea plant having all the physiological and morphological characteristics of a chickpea plant produced by growing 'NC-007' chickpea seed.

In another aspect, the present invention is further directed to tissue culture or cells derived from 'NC-007' chickpea plants. In one embodiment, the present invention provides a tissue culture of protoplasts or regenerable cells from a plant or parts thereof, produced by growing seed designated 'NC-007'. In another embodiment, the present invention provides a chickpea plant regenerated from tissue culture, wherein the plant has all of the morphological and physiological characteristics of a chickpea plant produced by growing seed designated as 'NC-007' having ATCC Accession Number X7.

In still another aspect, the present invention is directed to an $F_1$ hybrid chickpea seed, a plant grown from the seed, or a plant part isolated therefrom having 'NC-007' as a parent, wherein 'NC-007' is grown from 'NC-007' chickpea seed having ATCC Accession Number X7. In another embodiment, the present invention is directed to a pollen grain, an ovule, a protoplast, a cell, an embryo, a cotyledon, a hypocotyl, a meristem, a root, a pistil, an anther, a flower, a stem, a pod, a leaf, a petiole, or a portion thereof isolated from an $F_1$ hybrid chickpea plant, having 'NC-007' as a parent, wherein 'NC-007' is grown from 'NC-007' chickpea seed having ATCC Accession Number X7.

In another aspect, the present invention is directed to a method of making chickpea seeds, said method comprising crossing the chickpea plant produced by growing 'NC-007' chickpea seed with another chickpea plant and harvesting seed therefrom.

In a further aspect, the present invention is directed to a method of making the chickpea variety 'NC-007', said method comprising selecting seeds from the cross of one 'NC-007' plant with another 'NC-007' plant, a sample of 'NC-007' chickpea seed having been deposited under ATCC Accession Number X7.

In another aspect, the present invention is directed to a method of producing a seed of a 'NC-007'-derived chickpea plant, comprising the steps of a) crossing a chickpea variety designated as 'NC-007' having ATCC Accession Number X7, with itself or a second chickpea plant; and b) allowing seed of a 'NC-007'-derived chickpea plant to form. In one embodiment, the method of producing a seed of a 'NC-007'-derived chickpea plant further comprises the steps of c) crossing a plant grown from 'NC-007'-derived chickpea seed with itself or a second chickpea plant to yield additional 'NC-007'-derived chickpea seed; d) growing the additional 'NC-007'-derived chickpea seed of step (c) to yield additional 'NC-007'-derived chickpea plants; and e) repeating steps (c) and (d) for an additional 3-10 generations to generate further 'NC-007'-derived chickpea plants.

In another aspect, the present invention is directed to methods of producing a chickpea plant having one or more value-added traits by introducing one or more genes conferring one or more value-added traits into a chickpea plant produced by growing 'NC-007' chickpea seed having ATCC Accession Number X7. Some embodiments are directed to chickpea plants having one or more value-added trait produced by such methods. In one embodiment, the present invention provides methods of producing an herbicide resistant chickpea plant by introducing a gene conferring herbicide resistance into a chickpea plant produced by growing 'NC-007' chickpea seed, and to herbicide resistant chickpea plants produced by such methods. In another embodiment, the present invention provides methods of producing a pest or insect resistant chickpea plant by introducing a gene conferring pest or insect resistance into a chickpea plant produced by growing 'NC-007' chickpea seed, and to pest or insect resistant chickpea plants produced by such methods. In yet another embodiment, the present invention provides methods of producing a disease resistant chickpea plant by introducing a gene conferring disease resistance into a chickpea plant produced by growing 'NC-007' chickpea seed, and to disease resistant chickpea plants produced by such methods.

In yet another aspect, the present invention provides a method of producing a commodity plant product, comprising obtaining the chickpea plant produced by growing 'NC-007' chickpea seed having ATCC Accession Number X7, or a plant part thereof, and producing said commodity plant product therefrom. In one embodiment, the plant part is a seed. In one embodiment, the commodity plant product is a protein isolate, a protein concentrate, a texturized protein product, a meal, a flour, a starch, a fiber, or an oil. In one embodiment, the present invention is further directed to packaging material containing 'NC-007' plant parts or a commodity plant product produced therefrom. The 'NC-007' plant parts, or commodity plant products produced therefrom, may be combined with other plant parts of other plant varieties, other commodity plant products, food products, food ingredients, and the like.

In one aspect, the present invention is directed to chickpea seed designated as 'NC-008' having ATCC Accession Number X8. In one embodiment, the present invention is directed to a chickpea plant and parts isolated therefrom produced by growing 'NC-008' chickpea seed. In another embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from 'NC-008' chickpea plants. In a certain embodiment, the present invention is further directed to a chickpea seed isolated from 'NC-008' chickpea plants.

In another aspect, the present invention is directed to a chickpea plant and parts isolated therefrom having all the physiological and morphological characteristics of a chickpea plant produced by growing 'NC-008' chickpea seed having ATCC Accession Number X8. In one embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from a chickpea plant having all the physiological and morphological characteristics of a chickpea plant produced by growing 'NC-008' chickpea seed. In a certain embodiment, the present invention is further directed to a chickpea seed isolated from a chickpea plant having all the physiological and morphological characteristics of a chickpea plant produced by growing 'NC-008' chickpea seed.

In another aspect, the present invention is further directed to tissue culture or cells derived from 'NC-008' chickpea plants. In one embodiment, the present invention provides a tissue culture of protoplasts or regenerable cells from a plant or parts thereof, produced by growing seed designated 'NC-008'. In another embodiment, the present invention provides a chickpea plant regenerated from tissue culture, wherein the plant has all of the morphological and physiological characteristics of a chickpea plant produced by growing seed designated as 'NC-008' having ATCC Accession Number X8.

In still another aspect, the present invention is directed to an $F_1$ hybrid chickpea seed, a plant grown from the seed, or a plant part isolated therefrom having 'NC-008' as a parent, wherein 'NC-008' is grown from 'NC-008' chickpea seed having ATCC Accession Number X8. In another embodiment, the present invention is directed to a pollen grain, an ovule, a protoplast, a cell, an embryo, a cotyledon, a hypocotyl, a meristem, a root, a pistil, an anther, a flower, a stem, a pod, a leaf, a petiole, or a portion thereof isolated from an $F_1$ hybrid chickpea plant, having 'NC-008' as a parent, wherein 'NC-008' is grown from 'NC-008' chickpea seed having ATCC Accession Number X8.

In another aspect, the present invention is directed to a method of making chickpea seeds, said method comprising crossing the chickpea plant produced by growing 'NC-008' chickpea seed with another chickpea plant and harvesting seed therefrom.

In a further aspect, the present invention is directed to a method of making the chickpea variety 'NC-008', said method comprising selecting seeds from the cross of one 'NC-008' plant with another 'NC-008' plant, a sample of 'NC-008' chickpea seed having been deposited under ATCC Accession Number X8.

In another aspect, the present invention is directed to a method of producing a seed of a 'NC-008'-derived chickpea plant, comprising the steps of a) crossing a chickpea variety designated as 'NC-008' having ATCC Accession Number X8, with itself or a second chickpea plant; and b) allowing seed of a 'NC-008'-derived chickpea plant to form. In one embodiment, the method of producing a seed of a 'NC-008'-derived chickpea plant further comprises the steps of c) crossing a plant grown from 'NC-008'-derived chickpea seed with itself or a second chickpea plant to yield additional 'NC-008'-derived chickpea seed; d) growing the additional 'NC-008'-derived chickpea seed of step (c) to yield additional 'NC-008'-derived chickpea plants; and e) repeating steps (c) and (d) for an additional 3-10 generations to generate further 'NC-008'-derived chickpea plants.

In another aspect, the present invention is directed to methods of producing a chickpea plant having one or more value-added traits by introducing one or more genes conferring one or more value-added traits into a chickpea plant produced by growing 'NC-008' chickpea seed having ATCC Accession Number X8. Some embodiments are directed to chickpea plants having one or more value-added trait produced by such methods. In one embodiment, the present invention provides methods of producing an herbicide resistant chickpea plant by introducing a gene conferring herbicide resistance into a chickpea plant produced by growing 'NC-008' chickpea seed, and to herbicide resistant chickpea plants produced by such methods. In another embodiment, the present invention provides methods of producing a pest or insect resistant chickpea plant by introducing a gene conferring pest or insect resistance into a chickpea plant produced by growing 'NC-008' chickpea seed, and to pest or insect resistant chickpea plants produced by such methods. In yet another embodiment, the present invention provides methods of producing a disease resistant chickpea plant by introducing a gene conferring disease resistance into a chickpea plant produced by growing 'NC-008' chickpea seed, and to disease resistant chickpea plants produced by such methods.

In yet another aspect, the present invention provides a method of producing a commodity plant product, comprising obtaining the chickpea plant produced by growing 'NC-008' chickpea seed having ATCC Accession Number X8, or a plant part thereof, and producing said commodity plant product therefrom. In one embodiment, the plant part is a seed. In one embodiment, the commodity plant product is a protein isolate, a protein concentrate, a texturized protein product, a meal, a flour, a starch, a fiber, or an oil. In one embodiment, the present invention is further directed to packaging material containing 'NC-008' plant parts or a commodity plant product produced therefrom. The 'NC-008' plant parts, or commodity plant products produced therefrom, may be combined with other plant parts of other plant varieties, other commodity plant products, food products, food ingredients, and the like.

In one aspect, the present invention is directed to chickpea seed designated as 'NC-009' having ATCC Accession Number X9. In one embodiment, the present invention is directed to a chickpea plant and parts isolated therefrom produced by growing 'NC-009' chickpea seed. In another embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from 'NC-009' chickpea plants. In a certain embodiment, the present invention is further directed to a chickpea seed isolated from 'NC-009' chickpea plants.

In another aspect, the present invention is directed to a chickpea plant and parts isolated therefrom having all the physiological and morphological characteristics of a chickpea plant produced by growing 'NC-009' chickpea seed having ATCC Accession Number X9. In one embodiment, the present invention is further directed to a chickpea pollen grain, ovule, protoplast, cell, embryo, cotyledon, hypocotyl, meristem, root, pistil, anther, flower, stem, pod, leaf, and/or petiole isolated from a chickpea plant having all the physiological and morphological characteristics of a chickpea plant produced by growing 'NC-009' chickpea seed. In a certain embodiment, the present invention is further directed to a chickpea seed isolated from a chickpea plant having all the physiological and morphological characteristics of a chickpea plant produced by growing 'NC-009' chickpea seed.

In another aspect, the present invention is further directed to tissue culture or cells derived from 'NC-009' chickpea plants. In one embodiment, the present invention provides a tissue culture of protoplasts or regenerable cells from a plant or parts thereof, produced by growing seed designated 'NC-009'. In another embodiment, the present invention provides a chickpea plant regenerated from tissue culture, wherein the plant has all of the morphological and physiological characteristics of a chickpea plant produced by growing seed designated as 'NC-009' having ATCC Accession Number X9.

In still another aspect, the present invention is directed to an $F_1$ hybrid chickpea seed, a plant grown from the seed, or a plant part isolated therefrom having 'NC-009' as a parent, wherein 'NC-009' is grown from 'NC-009' chickpea seed having ATCC Accession Number X9. In another embodiment, the present invention is directed to a pollen grain, an ovule, a protoplast, a cell, an embryo, a cotyledon, a hypocotyl, a meristem, a root, a pistil, an anther, a flower, a stem, a pod, a leaf, a petiole, or a portion thereof isolated from an $F_1$ hybrid chickpea plant, having 'NC-009' as a parent, wherein 'NC-009' is grown from 'NC-009' chickpea seed having ATCC Accession Number X9.

In another aspect, the present invention is directed to a method of making chickpea seeds, said method comprising crossing the chickpea plant produced by growing 'NC-009' chickpea seed with another chickpea plant and harvesting seed therefrom.

In a further aspect, the present invention is directed to a method of making the chickpea variety 'NC-009', said method comprising selecting seeds from the cross of one 'NC-009' plant with another 'NC-009' plant, a sample of 'NC-009' chickpea seed having been deposited under ATCC Accession Number X9.

In another aspect, the present invention is directed to a method of producing a seed of a 'NC-009'-derived chickpea plant, comprising the steps of a) crossing a chickpea variety designated as 'NC-009' having ATCC Accession Number X9, with itself or a second chickpea plant; and b) allowing seed of a 'NC-009'-derived chickpea plant to form. In one embodiment, the method of producing a seed of a 'NC-009'-derived chickpea plant further comprises the steps of c) crossing a plant grown from 'NC-009'-derived chickpea seed with itself or a second chickpea plant to yield additional 'NC-009'-derived chickpea seed; d) growing the additional 'NC-009'-derived chickpea seed of step (c) to yield additional 'NC-009'-derived chickpea plants; and e) repeating steps (c) and (d) for an additional 3-10 generations to generate further 'NC-009'-derived chickpea plants.

In another aspect, the present invention is directed to methods of producing a chickpea plant having one or more value-added traits by introducing one or more genes conferring one or more value-added traits into a chickpea plant produced by growing 'NC-009' chickpea seed having ATCC Accession Number X9. Some embodiments are directed to chickpea plants having one or more value-added trait produced by such methods. In one embodiment, the present invention provides methods of producing an herbicide resistant chickpea plant by introducing a gene conferring herbicide resistance into a chickpea plant produced by growing 'NC-009' chickpea seed, and to herbicide resistant chickpea plants produced by such methods. In another embodiment, the present invention provides methods of producing a pest or insect resistant chickpea plant by introducing a gene conferring pest or insect resistance into a chickpea plant produced by growing 'NC-009' chickpea seed, and to pest or insect resistant chickpea plants produced by such methods. In yet another embodiment, the present invention provides methods of producing a disease resistant chickpea plant by introducing a gene conferring disease resistance into a chickpea plant produced by growing 'NC-009' chickpea seed, and to disease resistant chickpea plants produced by such methods.

In yet another aspect, the present invention provides a method of producing a commodity plant product, comprising obtaining the chickpea plant produced by growing 'NC-009' chickpea seed having ATCC Accession Number X9, or a plant part thereof, and producing said commodity plant product therefrom. In one embodiment, the plant part is a seed. In one embodiment, the commodity plant product is a protein isolate, a protein concentrate, a texturized protein product, a meal, a flour, a starch, a fiber, or an oil. In one embodiment, the present invention is further directed to packaging material containing 'NC-009' plant parts or a commodity plant product produced therefrom. The 'NC-009' plant parts, or commodity plant products produced therefrom, may be combined with other plant parts of other plant varieties, other commodity plant products, food products, food ingredients, and the like.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1A shows seeds of chickpea variety 'NC-001'. FIG. 1B shows dry plants of chickpea variety 'NC-001', including the pods of the variety.

FIG. 2A shows seeds of chickpea variety 'NC-002'. FIG. 2B shows dry plants of chickpea variety 'NC-002', including the pods of the variety.

FIG. 3A shows top, bottom, and side views of seeds of chickpea variety 'NC-003'. FIG. 3B shows plants of the chickpea variety 'NC-003', including the leaves and pods of the variety.

FIG. 4A shows seeds of chickpea variety 'NC-004'. FIG. 4B shows top, bottom, and side views of seeds of chickpea variety 'NC-004'. FIG. 4C shows plants of the chickpea variety 'NC-004', including the leaves, flowers, and pods of the variety.

FIG. 5A shows seeds of chickpea variety 'NC-005'. FIG. 5B shows top, bottom, and side views of seeds of chickpea variety 'NC-005'. FIG. 5C shows plants of the chickpea variety 'NC-005', including the leaves and pods of the variety.

FIG. 9A shows seeds of chickpea variety 'NC-009'. FIG. 9B shows plants of the chickpea variety 'NC-009', including the leaves and pods of the variety.

DETAILED DESCRIPTION OF THE INVENTION

Figure 1A:
FIGS. 1A-1B show seeds and plants of chickpea variety 'NC-001'.

There are numerous steps in the development of novel, desirable chickpea varieties. Plant breeding begins with the analysis of problems and weaknesses of current chickpea varieties, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include seed size and weight, number of seeds per pod, seed yield, seed coloration, seed coat thickness, seed protein quantity, seed protein content, seed protein functional properties, overall seed nutritional content, degree of nodulation and nitrogen fixation, drought tolerance, heat tolerance, tolerance to aluminum in acid soils, time to maturity, plant architecture, agronomic quality, and the like.

Choice of breeding or selection methods can depend on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. For traits that are linked to environmental conditions (e.g. drought tolerance, heat tolerance, etc.) selection should be based on mean values obtained from plants evaluated under the relevant specific environmental conditions (e.g. drought, heat, etc.). Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure.

Evaluation criteria vary depending on the goal and objectives, and can include gain from selection per year based on comparisons to an appropriate standard, the overall value of the advanced breeding lines, and the number of successful varieties produced per unit of input (e.g., per year, per dollar expended, etc.).

Promising advanced breeding lines may be thoroughly tested and compared to appropriate standards in environments representative of the commercial target area(s) for at least three years. The best lines can then be candidates for new commercial varieties. Those still deficient in a few traits may be used as parents to produce new populations for further selection. These processes, which lead to the final step of marketing and distribution, may take from ten to twenty years from the time the first cross or selection is made, though genomic selection and accelerated plant life cycles can shorten this timeline.

One goal of chickpea plant breeding is to develop new, unique, and genetically superior chickpea varieties. A breeder can initially select and cross two or more parental lines, followed by repeated selfing and selection, producing many new genetic combinations. Moreover, a breeder can generate multiple different genetic combinations by crossing, selfing, introducing mutations, and introducing transgenes via transformation. A plant breeder can then select which germplasms to advance to the next generation. These germplasms may then be grown under different geographical, climatic, and soil conditions, and further selections can be made during, and at the end of, the growing season.

The development of commercial chickpea varieties thus requires the development of parental chickpea varieties, the crossing of these varieties, and the evaluation of the crosses. Pedigree breeding and recurrent selection breeding methods may be used to develop varieties from breeding populations. Breeding programs can be used to combine desirable traits from two or more varieties or various broad-based sources into breeding pools from which new varieties are developed by selfing and selection of desired phenotypes. For example, introgression of genetic material from crop wild relatives, landraces, and the like into crop breeding pools can increase the genetic diversity of the pool and result in improved varieties. The new varieties are crossed with other varieties and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques known in the art that are available for the analysis, comparison and characterization of plant genotype. Such techniques include, without limitation, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs, which are also referred to as Microsatellites), Single Nucleotide Polymorphisms (SNPs) and insertion-deletions (indels).

Molecular markers can also be used during the breeding process for the selection of qualitative and quantitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Many plant traits are affected by multiple individual genes, and breeding based on genotyping can effectively construct complex combinations of different genes and their alleles. The terms chickpea variety, plant, hybrid, cultivar, or line are used in the context of the present invention and also include plants with two or more genes intentionally combined. In some cases such genes may bring different desired traits, for example herbicide resistance and disease resistance, into a single genetic background. In other cases, multiple genes may be combined to impact the value of a single trait through additivity or other gene interactions (e.g. epistasis). Genomic selection is a breeding method for multi-gene traits. Genomic selection uses statistical and computational methods in conjunction with molecular marker data to partition trait values to multiple genes, genome-wide. Partitioning trait values to multiple molecular makers and their interactions is the basis of molecular breeding methods that create varieties with desired gene combinations and traits. Genomic assisted introgression may be used to breed varieties with improvements in multi-gene traits, including, but not limited to, plant architecture, seed coat characteristics (e.g. thickness), flowering time, time to maturity, seed protein quantity, seed protein content, seed protein composition, other seed chemistries, seed functional properties, overall seed nutritional content, the presence or amount of pro- and anti-nutritional factors, degree of nodulation and nitrogen fixation, drought tolerance, heat tolerance, tolerance to aluminum in acid soils, yield, agronomic quality, and the like.

Mutation breeding may also be used to introduce new traits into chickpea varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.,* 77:889-892 (1989).

Additional non-limiting examples of breeding methods that may be used include, without limitation, those found in Allard, "Principles of plant breeding," John Wiley & Sons, NY, University of California, Davis, Calif., 50-98, 1960; Simmonds, "Principles of crop improvement." Longman, Inc., NY, 369-399, 1979; Sneep and Hendriksen, "Plant breeding perspectives," Wageningen (ed), Center for Agricultural Publishing and Documentation, 1979; Poehlman and Sleper, "Breeding Field Crops" Iowa State University Press, Ames, 1995; and Sprague and Dudley, eds., *Corn and Improvement,* 5th ed., 2006; Crossa et al. Genomic selection in plant breeding: methods, models and perspectives. Trends in Plant Sciences 22(11):961-975, 2017; Watson et al. Speed breeding is a powerful tool to accelerate crop research and breeding. Nature Plants.4:23-29, 2017.

Definitions

Backcrossing. Backcrossing is a process in which a breeder repeatedly crosses hybrid progeny back to one of the parents, for example, a first generation hybrid F₁ with one of the parental genotypes of the F₁ hybrid.

Commodity plant product. A product derived from a plant, or a plant part thereof, that is used as a commodity material in industry or food production. For example, commodity plant products of chickpeas may include protein isolate, protein concentrate, meal, flour, or oil derived from chickpeas.

Essentially all the physiological and morphological characteristics. A plant having essentially all the physiological and morphological characteristics means a plant having the physiological and morphological characteristics of the recurrent parent, except for the characteristics derived from the converted gene(s).

F₁ hybrid. A first filial generation plant resulting from the seed of a cross of two genetically distinct parent plants.

Fourier-Transformed Near Infrared (FT-NIR) spectroscopy. An analysis method that uses the NIR region of the electromagnetic spectrum (800-2,500 nm). It measures the absorption or reflectance of light by a sample across the NIR region to create an NIR spectrum. The light absorption by a sample at a specific wavelength is a function both of the functional groups (e.g. CH, NH or OH groups) and chemical bonds in that material that absorb light energy differently. An absorption spectrum can therefore be used to both identify and quantitate the material in a sample. An FT-NIR model is generated to predict the protein content in chickpea flour. Spectra are first created for flour samples with known protein concentrations. Protein content of calibration samples are obtained by third party laboratories using AOAC approved methods (i.e., DUMAS). Subsequently, statistical modeling identifies specific regions of these spectra where intensities correlate with the empirically determined protein concentrations. These models are used to extrapolate the protein content of unknown flour samples by analyzing their own NIR spectra at the relevant wavelengths.

Gene. As used herein, "gene" refers to a segment of nucleic acid, including, but not limited to, protein-coding regions. A gene can be introduced into a genome of a species, whether from a different species or from the same species, using transformation or various breeding methods.

Mature seed weight. The weight of chickpea seed after it has dried as a result of typical drying processes prior to harvest. As used herein, mature seed weight refers to the weight of chickpea seed prior to any further drying after harvest (for example, to remove any remaining dry seed moisture), and therefore may comprise some residual moisture.

Propagate. To "propagate" a plant means to reproduce the plant by means including, but not limited to, seeds, cuttings, divisions, tissue culture, embryo culture or other in vitro method.

Recombinant inbred line. A plant line generated by crossing two distinct parent plant lines to produce F₁ progeny, followed by repeated self-pollination of one or more of the F₁ progeny to produce one or more distinct, stable, inbred lines comprising genetic material from both of the parent lines of the original cross.

Regeneration. As used herein, "regeneration" refers to the development of a plant from tissue culture.

Seed protein content. The amount of protein in an unprocessed seed expressed as a percentage of the total weight of the mature seed. Seed protein content is determined using biochemical assays including, but not limited to, combustion elemental analysis methods (e.g. the Total Nitrogen Combustion Method, also known as the Dumas method), Fourier transform near-infrared spectroscopy (FT-NIR), or other methods using fluorescent or spectrophotometric detection. As used herein, seed protein content is expressed as a percent of mature seed weight without the seed coat (e.g. after seed is removed from the seed coat by dehulling, or with correction for the retained seed coat).

Single gene converted. As used herein, "single gene converted" or "conversion plant" refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Time to dry seed maturity. The period required for growth, blooming, pod formation, seed maturation, and complete pod and seed drying of a chickpea plant. Time to dry seed maturity is typically measured from the date of planting to the date that all or essentially all of the pods on the chickpea plant are dry. Essentially all of the pods on the chickpea plant are dry when the vast majority of the pods on the plant are fully dry, even if some pods on the plant are not fully dry due to, for example, secondary growth triggered by environmental conditions. Drying may be facilitated prior to harvest by use of herbicides that kill the mother plant and prevent further extraction of moisture from the soil.

Tissue culture. A composition comprising isolated cells of the same or a different type, or a collection of such cells organized into parts of a plant.

Total Nitrogen Combustion Method. A method of measuring protein content in plant material, also commonly known as the Dumas method. First, the total nitrogen content of a sample of a plant or plant part is analyzed via flash combustion, which converts all nitrogen in the sample to combustion gases (e.g. N₂, NOx, etc.). These combustion gases are then separated from the other combustion gases and detected, using, for example, thermal conductivity/infrared detection or gas chromatography/thermal conductivity detection. Then, the total nitrogen content is converted to crude protein content using a conversion factor, which is typically 6.25 for plant and/or feed materials. These methods are described in, for example, AOAC Official Methods 972.43 and 990.03 in Official Methods of Analysis of AOAC International, 18th edition, Revision 1, 2006.

Overview of the Variety 'NC-001'

Figure 1B:
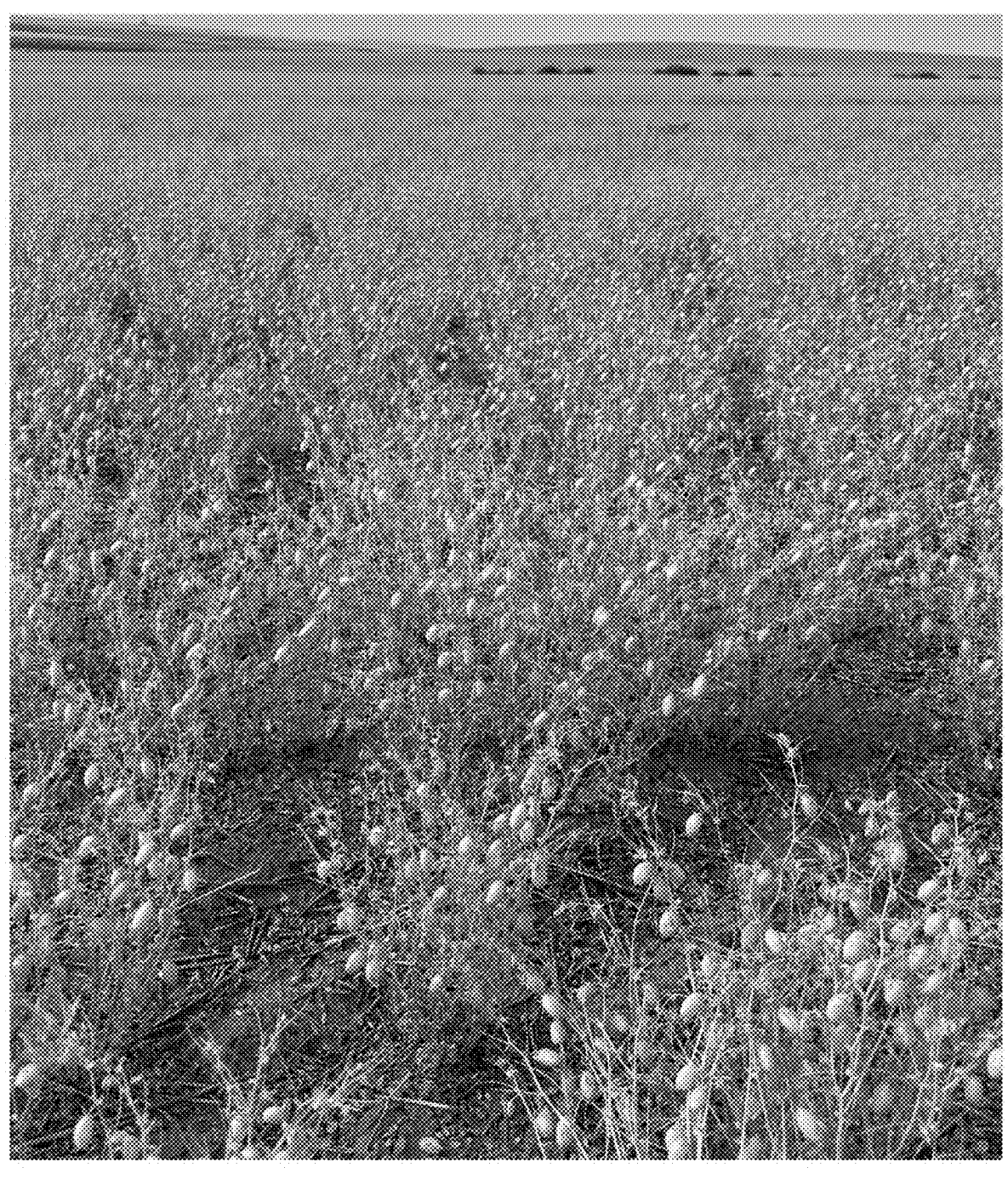

Chickpea variety 'NC-001' is a genetically unique chickpea plant exhibiting reddish dark brown seeds with spots and a seed protein content of 31.5%. Chickpea variety 'NC-001' is a recombinant inbred line resulting from a controlled cross followed by numerous generations of self-pollination and was selected for its seed protein content. Specifically, chickpea variety 'NC-001' is the result of crossing the female variety 'NCP-002', also known as the commodity variety 'CDC Consul' (no patent or PVP Certificate), and the male variety 'NCP-001' (no patent or PVP Certificate). Specifically, 'NCP-002' and 'NCP-001' were initially crossed in June 2015. Offspring from this cross were first evaluated in small field plots in Davis, California in 2020 using selection criteria of overall yield, plant architecture, plant height, flower time, maturity time, and seed composition. A second field evaluation in small plots using the same selection criteria took place in Woodland, California in 2021. Field evaluation in large plots against other advanced lines using the same selection criteria was conducted in California, Idaho, and Montana in 2022. 'NC-001' was identified in August 2022 in California. Subsequently, 'NC-001' was bulked and grown in large-scale tests to ensure variety stability and performance in California and Montana in 2023 and in Montana and Washington in 2024. Chickpea variety 'NC-001' is propagated through self-pollination. FIG. 1A shows seeds of chickpea variety 'NC-001'. FIG. 1B shows dry plants of the chickpea variety 'NC-001', including the pods of the variety, and illustrates the semi-upright growth habit of the variety.

The variety 'NC-001' has shown uniformity and stability for the traits, within the limits of environmental influence for the traits. It has been self-pollinated a sufficient number of generations with careful attention to uniformity of plant type. It has been increased with continued observation for uniformity. No variant traits have been observed or are expected in variety 'NC-001'.

Objective Description of the Variety 'NC-001'

Table 1 provides a summary of chickpea variety 'NC-001' plant characteristics. These characteristics were observed in plants of the variety that were planted between early April to early May near Davis, California, U.S.A. and late April through mid May in western Montana, U.S.A. Trait measurements, color descriptions, and other phenotypical descriptions may deviate from the stated values and descriptions depending upon variation in environmental, seasonal, climatic, and cultural conditions. 'NC-001' has not been observed under all possible environmental conditions. The indicated protein content represents an average across twelve field trials including 44 data points. The protein data was collected using multiple protein test methods and moisture values, and then extrapolated for averaging purposes. Those of skill in the art will recognize that these are typical values that may vary due to environment and that other values that are substantially equivalent are within the scope of the invention. As used herein, "a chickpea plant having all the physiological and morphological characteristics of chickpea variety 'NC-001'" is a plant having the characteristics set forth in Table 1 when grown in the same environmental conditions.

TABLE 1

| Characteristic | Value |
| --- | --- |
| Plant Morphology and Growth | |
| Plant Height | 450 mm |
| Growth Habit | Semi-Upright |
| Time to Dry Seed Maturity | 90 days |
| Method of Propagation | Self-pollination |
| Time of Beginning of Flowering | 45 days |
| Flower Characteristics | |
| Flower Color | Purple |
| Pod and Seed Characteristics | |
| Pod: Number of Seeds | Mostly single seeded pods, some pods double seeded |
| Seed Color | Dark reddish brown with spots |
| Seed Weight (average calculated from 1000 seed weight) | 0.22 g |
| Seed Shape | Angular |
| Seed Surface | Moderate tuberculate, some roughness |
| Seed Ribbing | Weak |
| Seed Protein Content | 31.5% |

Overview of the Variety 'NC-002'

Figure 2A:
FIGS. 2A-2B show seeds and plants of chickpea variety 'NC-002'.
Figure 2B:
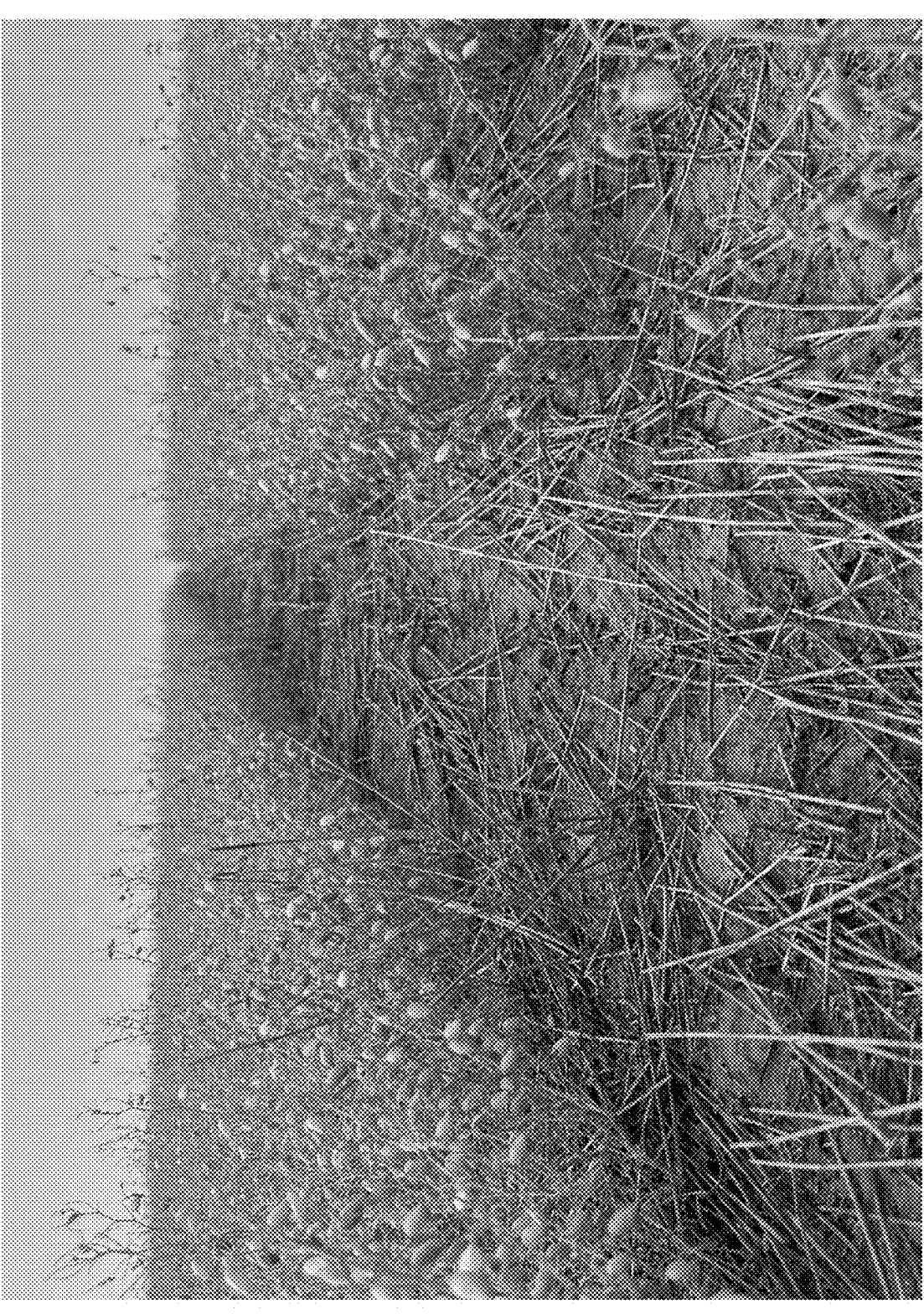

Chickpea variety 'NC-002' is a genetically unique chickpea plant exhibiting yellow to red tan seeds and a seed protein content of 30.0%. Chickpea variety 'NC-002' is a recombinant inbred line resulting from a controlled cross followed by numerous generations of self-pollination and was selected for its seed protein content. Chickpea variety 'NC-002' is propagated through self-pollination. FIG. 2A shows seeds of chickpea variety 'NC-002'. FIG. 2B shows dry plants of the chickpea variety 'NC-002', including the pods of the variety, and illustrates the semi-upright growth habit of the variety.

The variety 'NC-002' has shown uniformity and stability for the traits, within the limits of environmental influence for the traits. It has been self-pollinated a sufficient number of generations with careful attention to uniformity of plant type. It has been increased with continued observation for uniformity. No variant traits have been observed or are expected in variety 'NC-002'.

Objective Description of the Variety 'NC-002'

Table 2 provides a summary of chickpea variety 'NC-002' plant characteristics. These characteristics were observed in plants of the variety that were planted between early April through early May near Davis, California, U.S.A. and late April through mid May in western Montana, U.S.A. Trait measurements, color descriptions, and other phenotypical descriptions may deviate from the stated values and descriptions depending upon variation in environmental, seasonal, climatic, and cultural conditions. 'NC-002' has not been observed under all possible environmental conditions. The indicated protein content represents an average across twelve field trials including 57 data points. The protein data was collected using multiple protein test methods and moisture values, and then extrapolated for averaging purposes. Those of skill in the art will recognize that these are typical values that may vary due to environment and that other values that are substantially equivalent are within the scope of the invention. As used herein, "a chickpea plant having all the physiological and morphological characteristics of chickpea variety 'NC-002'" is a plant having the characteristics set forth in Table 2 when grown in the same environmental conditions.

TABLE 2

| Characteristic | Value |
| --- | --- |
| Plant Morphology and Growth | |
| Plant Height | 400 mm |
| Growth Habit | Semi-Upright |
| Time to Dry Seed Maturity | 100 days |
| Method of Propagation | Self-pollination |
| Time of Beginning of Flowering | 40 days |
| Flower Characteristics | |
| Flower Color | Purple |
| Pod and Seed Characteristics | |
| Pod: Number of Seeds | Mostly single seeded pods, some pods double seeded |
| Seed Color | Yellow/red tan |
| Seed Weight (average calculated from 1000 seed weight) | 0.129 g |
| Seed Shape | Angular |
| Seed Surface | Moderate tuberculate |
| Seed Ribbing | Medium |
| Seed Protein Content | 30.0% |

Overview of the Variety 'NC-003'

Figure 3A:
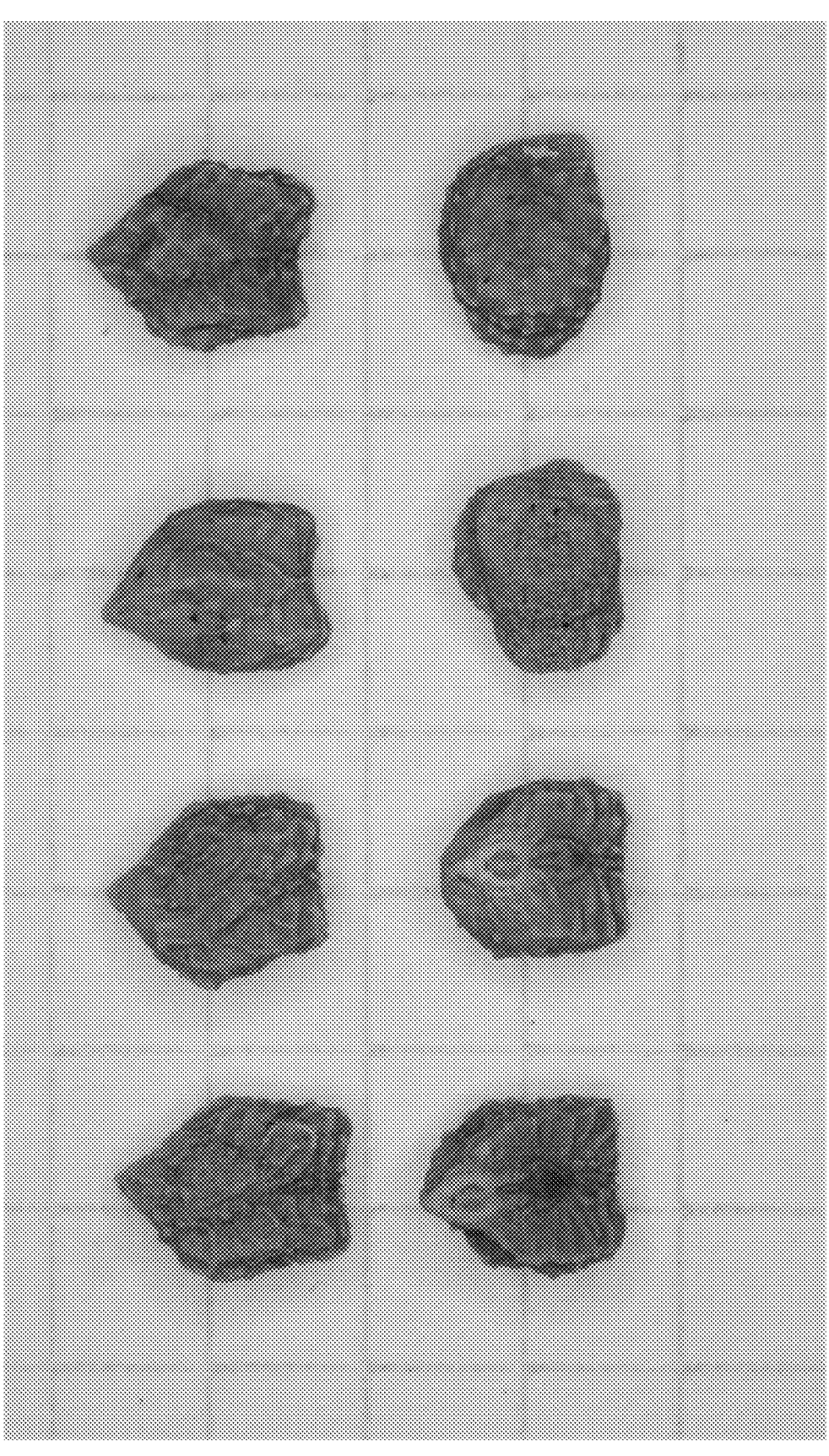
FIGS. 3A-3B show seeds and plants of chickpea variety 'NC-003'.
Figure 3B:

Chickpea variety 'NC-003' is a genetically unique chickpea plant exhibiting tan to reddish brown seeds and a seed protein content of 31.5%. Chickpea variety 'NC-003' is a recombinant inbred line resulting from a controlled cross followed by numerous generations of self-pollination and was selected for its seed protein content. Chickpea variety 'NC-003' is propagated through self-pollination. FIG. 3A shows top, bottom, and side views of seeds of chickpea variety 'NC-003'. FIG. 3B shows plants of the chickpea variety 'NC-003', including the leaves and pods of the variety, and illustrates the intermediate (between prostrate and upright) growth habit of the variety.

The variety 'NC-003' has shown uniformity and stability for the traits, within the limits of environmental influence for the traits. It has been self-pollinated a sufficient number of generations with careful attention to uniformity of plant type. It has been increased with continued observation for uniformity. No variant traits have been observed or are expected in variety 'NC-003'.

Objective Description of the Variety 'NC-003'

Table 3 provides a summary of chickpea variety 'NC-003' plant characteristics. These characteristics were observed in plants of the variety that were planted between early April through early May near Davis, California, U.S.A. and early May in western Montana, U.S.A. Trait measurements, color descriptions, and other phenotypical descriptions may deviate from the stated values and descriptions depending upon variation in environmental, seasonal, climatic, and cultural conditions. 'NC-003' has not been observed under all possible environmental conditions. The indicated protein content represents an average across seven field trials including 42 data points. The protein data was collected using multiple protein test methods and moisture values, and then extrapolated for averaging purposes. Those of skill in the art will recognize that these are typical values that may vary due to environment and that other values that are substantially equivalent are within the scope of the invention. As used herein, "a chickpea plant having all the physiological and morphological characteristics of chickpea variety 'NC-003'" is a plant having the characteristics set forth in Table 3 when grown in the same environmental conditions.

TABLE 3

| Characteristic | Value |
| --- | --- |
| Plant Morphology and Growth | |
| Plant Height | 350 mm |
| Growth Habit | Intermediate (between prostrate and upright) |
| Time to Dry Seed Maturity | 120-130 days |
| Method of Propagation | Self-pollination |
| Time of Flowering | 29 days |
| Flower Characteristics | |
| Flower Color | Purple |
| Pod and Seed Characteristics | |
| Pod: Number of Seeds | Mostly single seeded pods, some pods double seeded |
| Seed Color | Tan/reddish brown |
| Seed Weight (average calculated from 1000 seed weight) | 0.124 g |
| Seed Shape | Angular |
| Seed Surface | Tuberculate |
| Seed Ribbing | Strong |
| Seed Protein Content | 31.5% |

Overview of the Variety 'NC-004'

Figure 4A:
FIGS. 4A-4C show seeds and plants of chickpea variety 'NC-004'.
Figure 4B:
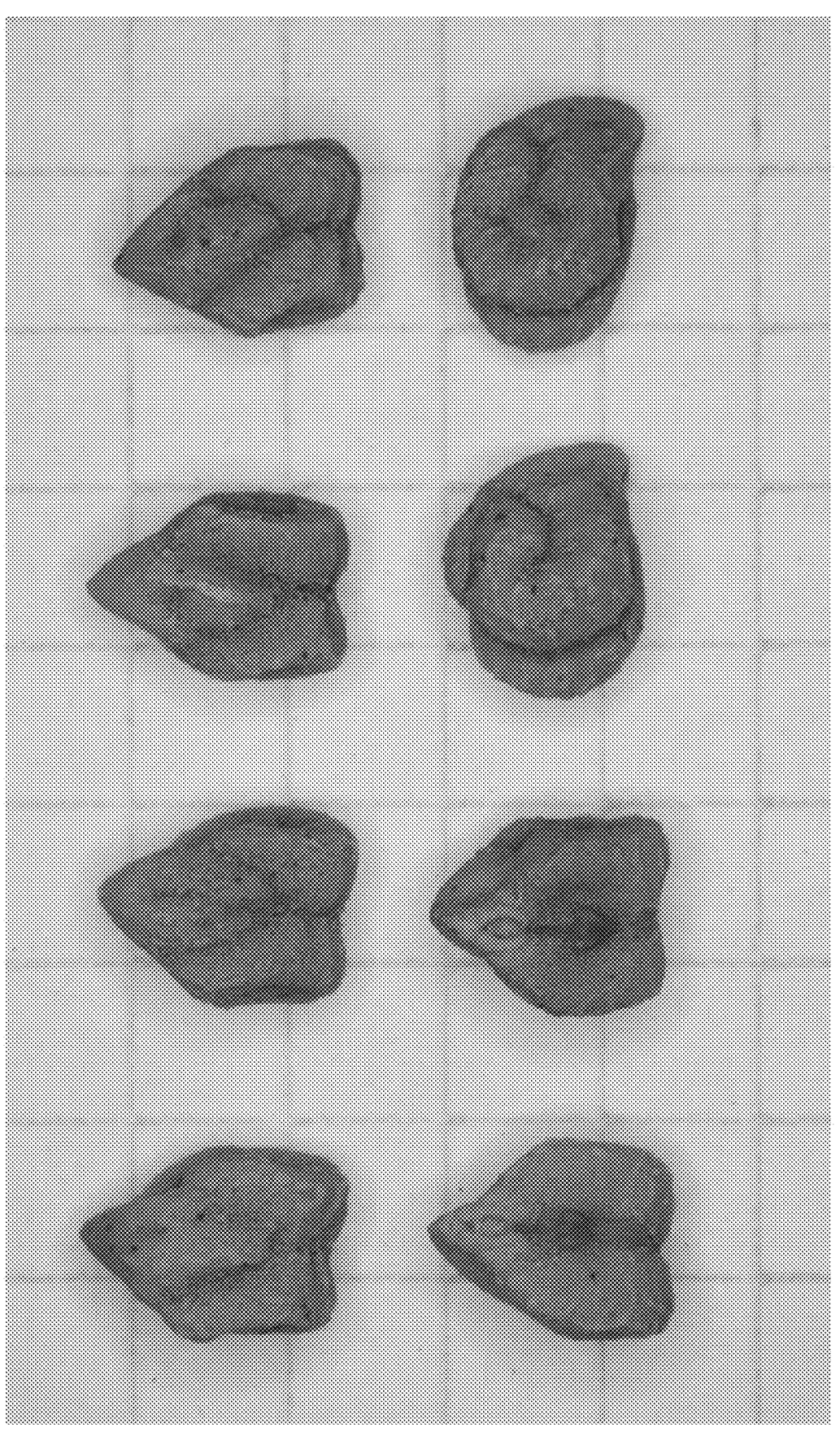
Figure 4C:
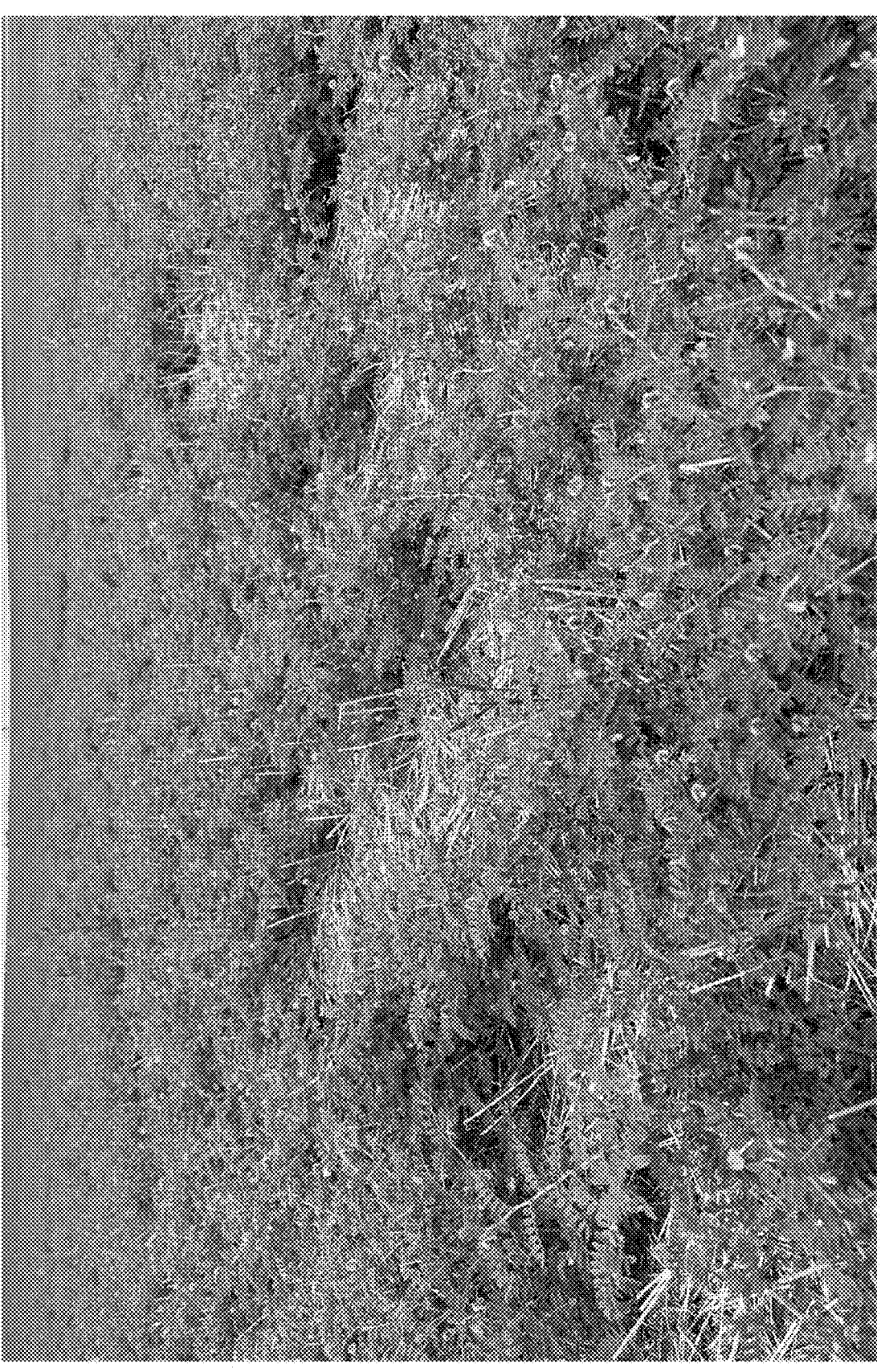

Chickpea variety 'NC-004' is a genetically unique chickpea plant exhibiting tan to reddish brown seeds with a few spots and a seed protein content of 31.5%. Chickpea variety 'NC-004' is a recombinant inbred line resulting from a controlled cross followed by numerous generations of self-pollination and was selected for its seed protein content. Chickpea variety 'NC-004' is propagated through self-pollination. FIG. 4A shows seeds of chickpea variety 'NC-004'. FIG. 4B shows top, bottom, and side views of seeds of chickpea variety 'NC-004'. FIG. 4C shows plants of the chickpea variety 'NC-004', including the leaves, flowers, and pods of the variety, and illustrates the intermediate (between prostrate and upright) growth habit of the variety.

The variety 'NC-004' has shown uniformity and stability for the traits, within the limits of environmental influence for the traits. It has been self-pollinated a sufficient number of generations with careful attention to uniformity of plant type. It has been increased with continued observation for uniformity. No variant traits have been observed or are expected in variety 'NC-004'.

Objective Description of the Variety 'NC-004'

Table 4 provides a summary of chickpea variety 'NC-004' plant characteristics. These characteristics were observed in plants of the variety that were planted between early April through early May near Davis, California, U.S.A. and late April through mid May in western Montana, U.S.A. Trait measurements, color descriptions, and other phenotypical descriptions may deviate from the stated values and descriptions depending upon variation in environmental, seasonal, climatic, and cultural conditions. 'NC-004' has not been observed under all possible environmental conditions. The indicated protein content represents an average across twelve field trials including 63 data points. The protein data was collected using multiple protein test methods and moisture values, and then extrapolated for averaging purposes. Those of skill in the art will recognize that these are typical values that may vary due to environment and that other values that are substantially equivalent are within the scope of the invention. As used herein, "a chickpea plant having all the physiological and morphological characteristics of chickpea variety 'NC-004'" is a plant having the characteristics set forth in Table 4 when grown in the same environmental conditions.

TABLE 4

| Characteristic | Value |
| --- | --- |
| Plant Morphology and Growth | |
| Plant Height | 300 mm |
| Growth Habit | Intermediate (between prostrate and upright) |
| Time to Dry Seed Maturity | 102 days |
| Method of Propagation | Self-pollination |
| Time of Beginning of Flowering | 40 days |
| Flower Characteristics | |
| Flower Color | Purple |
| Pod and Seed Characteristics | |
| Pod: Number of Seeds | Some double seeded pods, other pods single seeded |
| Seed Color | Tan/reddish brown |
| Seed Weight (average calculated from 1000 seed weight) | 0.133 g |
| Seed Shape | Angular |
| Seed Surface | Moderate tuberculate |
| Seed Ribbing | Weak |
| Seed Protein Content | 31.5% |

Overview of the Variety 'NC-005'

Figure 5A:
FIGS. 5A-5C show seeds and plants of chickpea variety 'NC-005'.
Figure 5B:
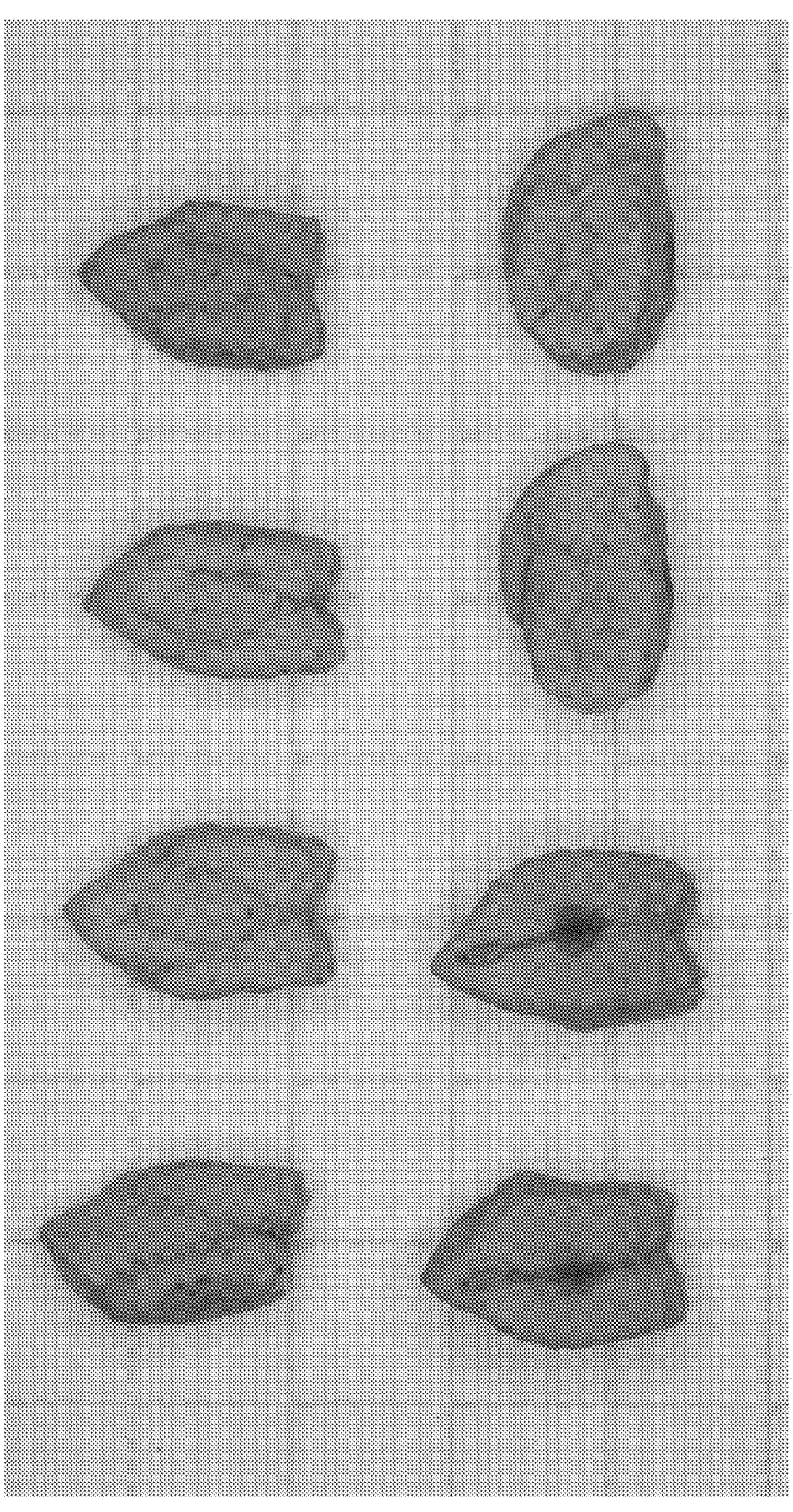
Figure 5C:

Chickpea variety 'NC-005' is a genetically unique chickpea plant exhibiting yellowish tan seeds with a few spots and a seed protein content of 30.5%. Chickpea variety 'NC-005' is a recombinant inbred line resulting from a controlled cross followed by numerous generations of self-pollination and was selected for its seed protein content. Chickpea variety 'NC-005' is propagated through self-pollination. FIG. 5A shows seeds of chickpea variety 'NC-005'. FIG. 5B shows top, bottom, and side views of seeds of chickpea variety 'NC-005'. FIG. 5C shows plants of the chickpea variety 'NC-005', including the leaves and pods of the variety, and illustrates the intermediate (between prostrate and upright) growth habit of the variety.

The variety 'NC-005' has shown uniformity and stability for the traits, within the limits of environmental influence for the traits. It has been self-pollinated a sufficient number of generations with careful attention to uniformity of plant type. It has been increased with continued observation for uniformity. No variant traits have been observed or are expected in variety 'NC-005'.

Objective Description of the Variety 'NC-005'

Table 5 provides a summary of chickpea variety 'NC-005' plant characteristics. These characteristics were observed in plants of the variety that were planted between early April through early May near Davis, California, U.S.A. Trait measurements, color descriptions, and other phenotypical descriptions may deviate from the stated values and descriptions depending upon variation in environmental, seasonal, climatic, and cultural conditions. 'NC-005' has not been observed under all possible environmental conditions. The indicated protein content represents an average across six field trials including 37 data points. The protein data was collected using multiple protein test methods and moisture values, and then extrapolated for averaging purposes. Those of skill in the art will recognize that these are typical values that may vary due to environment and that other values that are substantially equivalent are within the scope of the invention. As used herein, "a chickpea plant having all the physiological and morphological characteristics of chickpea variety 'NC-005'" is a plant having the characteristics set forth in Table 5 when grown in the same environmental conditions.

TABLE 5

| Characteristic | Value |
| --- | --- |
| Plant Morphology and Growth | |
| Plant Height | 270 mm |
| Growth Habit | Intermediate (between prostrate and upright) |
| Time to Dry Seed Maturity | 110 days |
| Method of Propagation | Self-pollination |
| Time of Beginning of Flowering | 47 days |
| Flower Characteristics | |
| Flower Color | Purple |
| Pod and Seed Characteristics | |
| Pod: Number of Seeds | Some double seeded pods, other pods single seeded |
| Seed Color | Yellowish tan |
| Seed Weight (average calculated from 1000 seed weight) | 0.12 g |
| Seed Shape | Angular |
| Seed Surface | Moderate tuberculate |
| Seed Ribbing | Medium |
| Seed Protein Content | 30.5% |

Overview of the Variety 'NC-006'

Figure 6:
FIG. 6 shows seeds of chickpea variety 'NC-006'.

Chickpea variety 'NC-006' is a genetically unique chickpea plant exhibiting medium brown seeds. Chickpea variety 'NC-006' is a recombinant inbred line resulting from a controlled cross followed by numerous generations of self-pollination and was selected for its seed protein content. Chickpea variety 'NC-006' is propagated through self-pollination. FIG. 6 shows seeds of chickpea variety 'NC-006'.

The variety 'NC-006' has shown uniformity and stability for the traits, within the limits of environmental influence for the traits. It has been self-pollinated a sufficient number of generations with careful attention to uniformity of plant type. It has been increased with continued observation for uniformity. No variant traits have been observed or are expected in variety 'NC-006'.

Objective Description of the Variety 'NC-006'

Table 6 provides a summary of chickpea variety 'NC-006' plant characteristics. These characteristics were observed in plants of the variety that were planted between early April through early May near Davis, California, U.S.A. Trait measurements, color descriptions, and other phenotypical descriptions may deviate from the stated values and descriptions depending upon variation in environmental, seasonal, climatic, and cultural conditions. 'NC-006' has not been observed under all possible environmental conditions. Those of skill in the art will recognize that these are typical values that may vary due to environment and that other values that are substantially equivalent are within the scope of the invention. As used herein, "a chickpea plant having all the physiological and morphological characteristics of chickpea variety 'NC-006'" is a plant having the characteristics set forth in Table 6 when grown in the same environmental conditions.

TABLE 6

| Characteristic | Value |
| --- | --- |
| Plant Morphology and Growth | |
| Plant Height | 360 mm |
| Growth Habit | Intermediate (between prostrate and upright) |
| Method of Propagation | Self-pollination |
| Pod and Seed Characteristics | |
| Pod: Number of Seeds | Mostly single seeded pods, other pods double seeded |
| Seed Color | Medium brown |
| Seed Weight (average calculated from 1000 seed weight) | 0.19 g |
| Seed Shape | Pea-shaped |
| Seed Surface | Smooth |
| Seed Ribbing | Very weak |

Overview of the Variety 'NC-007'

Figure 7:
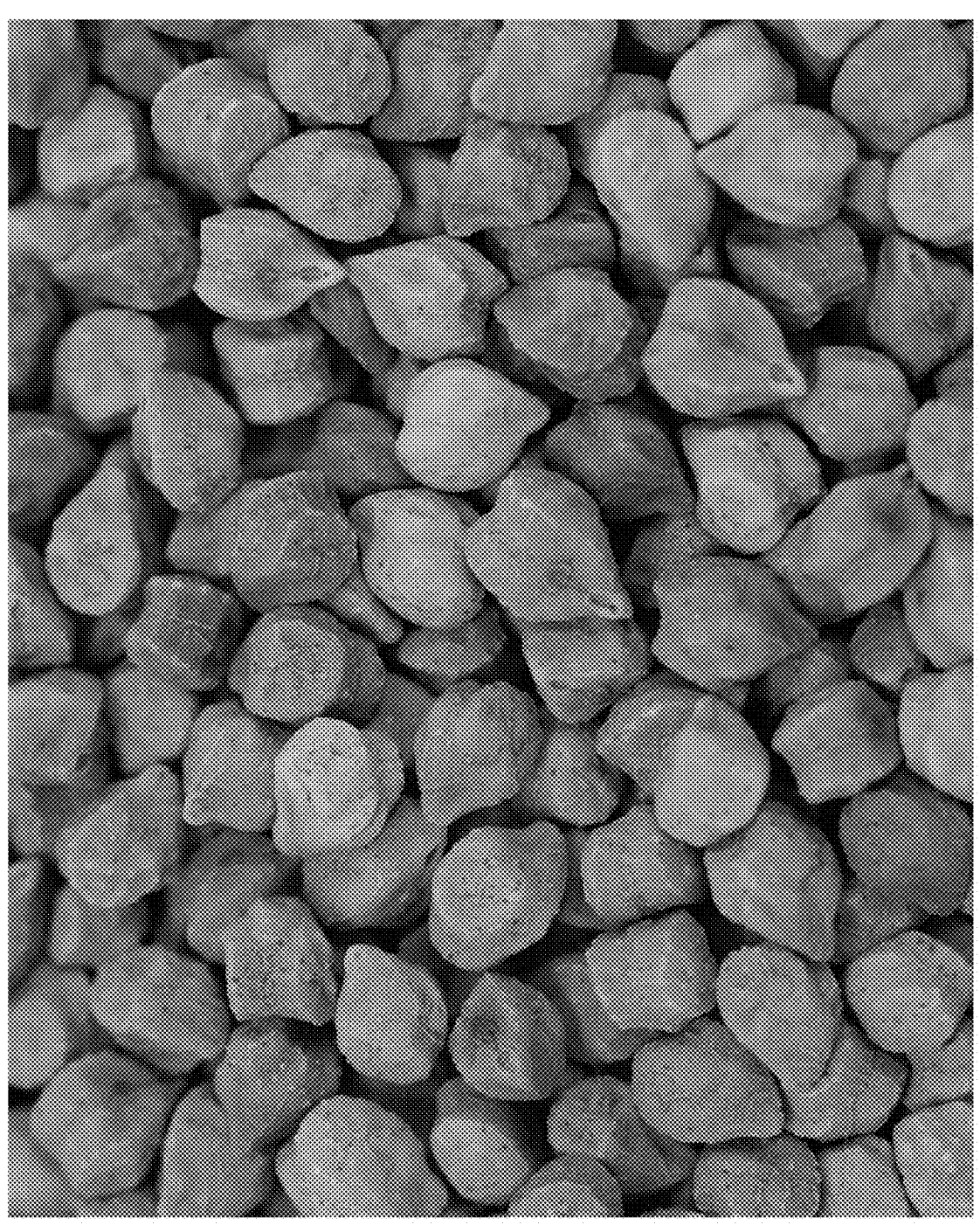
FIG. 7 shows seeds of chickpea variety 'NC-007'.

Chickpea variety 'NC-007' is a genetically unique chickpea plant exhibiting tan to reddish brown seeds and a seed protein content of 26%. Chickpea variety 'NC-007' is a recombinant inbred line resulting from a controlled cross followed by numerous generations of self-pollination and was selected for its seed protein content. Chickpea variety 'NC-007' is propagated through self-pollination. FIG. 7 shows seeds of chickpea variety 'NC-007'.

The variety 'NC-007' has shown uniformity and stability for the traits, within the limits of environmental influence for the traits. It has been self-pollinated a sufficient number of generations with careful attention to uniformity of plant type. It has been increased with continued observation for uniformity. No variant traits have been observed or are expected in variety 'NC-007'.

Objective Description of the Variety 'NC-007'

Table 7 provides a summary of chickpea variety 'NC-007' plant characteristics. These characteristics were observed in plants of the variety that were planted between early April through early May near Davis, California, U.S.A. Trait measurements, color descriptions, and other phenotypical descriptions may deviate from the stated values and descriptions depending upon variation in environmental, seasonal, climatic, and cultural conditions. 'NC-007' has not been observed under all possible environmental conditions. The indicated protein content represents an average across six field trials including 11 data points. The protein data was collected using multiple protein test methods and moisture values, and then extrapolated for averaging purposes. Those of skill in the art will recognize that these are typical values that may vary due to environment and that other values that are substantially equivalent are within the scope of the invention. As used herein, "a chickpea plant having all the physiological and morphological characteristics of chickpea variety 'NC-007'" is a plant having the characteristics set forth in Table 7 when grown in the same environmental conditions.

TABLE 7

| Characteristic | Value |
|---|---|
| Plant Morphology and Growth | |
| Plant Height | 300 mm |
| Growth Habit | Intermediate (between prostrate and upright) |
| Time to Dry Seed Maturity | 95 days |
| Method of Propagation | Self-pollination |
| Time of Beginning of Flowering | 40 days |
| Flower Characteristics | |
| Flower Color | Purple |
| Pod and Seed Characteristics | |
| Pod: Number of Seeds | Mostly single seeded pods, some pods double seeded |
| Seed Color | Tan/reddish brown |
| Seed Weight (average calculated from 1000 seed weight) | 0.149 g |
| Seed Shape | Intermediate |
| Seed Surface | Smooth |
| Seed Ribbing | Weak |
| Seed Protein Content | 26% |

Overview of the Variety 'NC-008'

Figure 8:
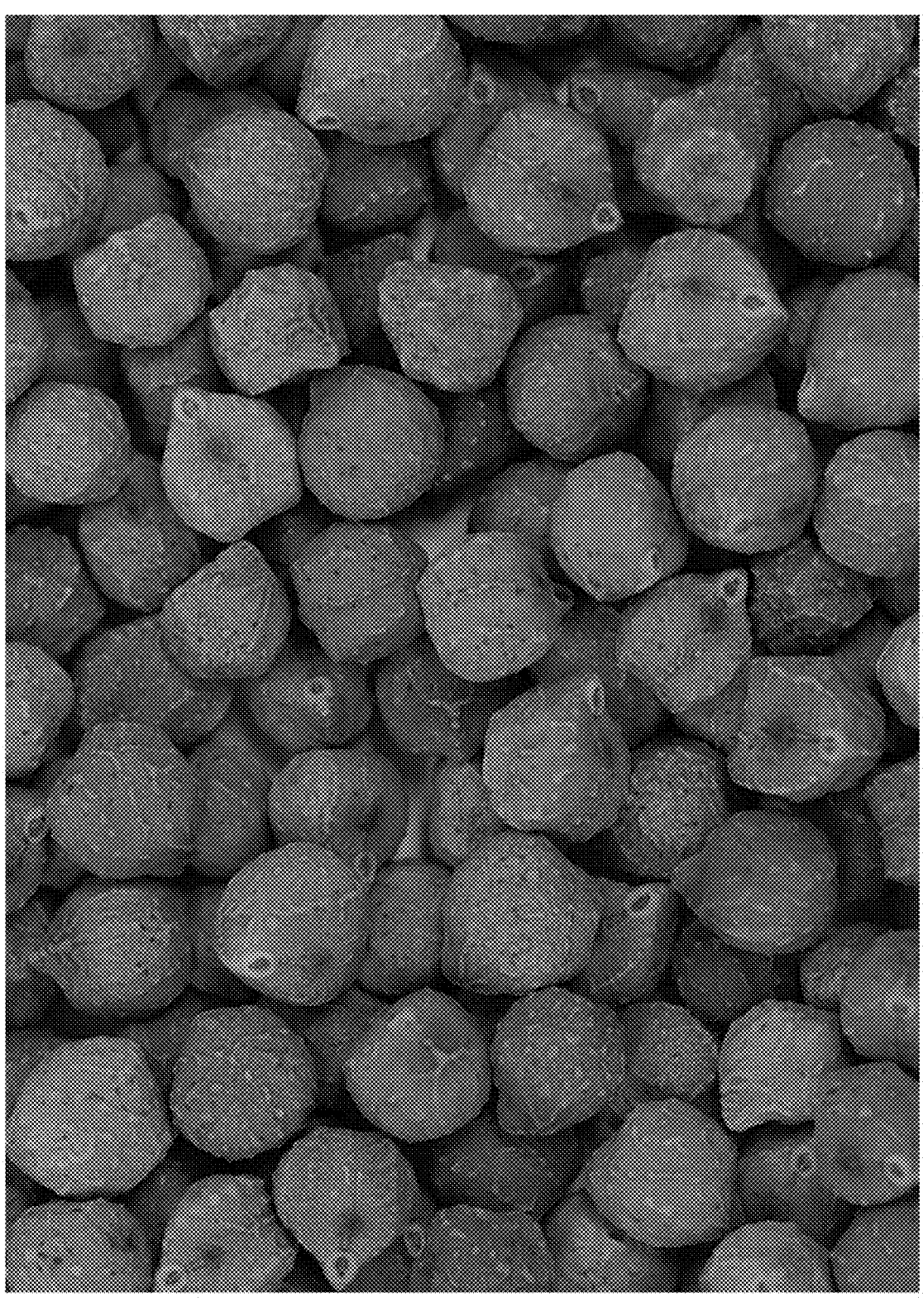
FIG. 8 shows seeds of chickpea variety 'NC-008'.

Chickpea variety 'NC-008' is a genetically unique chickpea plant exhibiting reddish brown seeds and a seed protein content of 24%. Chickpea variety 'NC-008' is a recombinant inbred line resulting from a controlled cross followed by numerous generations of self-pollination and was selected for its seed protein content. Chickpea variety 'NC-008' is propagated through self-pollination. FIG. 8 shows seeds of chickpea variety 'NC-008'.

The variety 'NC-008' has shown uniformity and stability for the traits, within the limits of environmental influence for the traits. It has been self-pollinated a sufficient number of generations with careful attention to uniformity of plant type. It has been increased with continued observation for uniformity. No variant traits have been observed or are expected in variety 'NC-008'.

Objective Description of the Variety 'NC-008'

Table 8 provides a summary of chickpea variety 'NC-008' plant characteristics. These characteristics were observed in plants of the variety that were planted between early April through early May near Davis, California, U.S.A. Trait measurements, color descriptions, and other phenotypical descriptions may deviate from the stated values and descriptions depending upon variation in environmental, seasonal, climatic, and cultural conditions. 'NC-008' has not been observed under all possible environmental conditions. The indicated protein content represents an average across six field trials including 12 data points. The protein data was collected using multiple protein test methods and moisture values, and then extrapolated for averaging purposes. Those of skill in the art will recognize that these are typical values that may vary due to environment and that other values that are substantially equivalent are within the scope of the invention. As used herein, "a chickpea plant having all the physiological and morphological characteristics of chickpea variety 'NC-008'" is a plant having the characteristics set forth in Table 8 when grown in the same environmental conditions.

TABLE 8

| Characteristic | Value |
|---|---|
| Plant Morphology and Growth | |
| Plant Height | 330 mm |
| Growth Habit | Upright |
| Time to Dry Seed Maturity | 95 days |
| Method of Propagation | Self-pollination |
| Time of Beginning of Flowering | 37 days |
| Flower Characteristics | |
| Flower Color | Purple |
| Pod and Seed Characteristics | |
| Pod: Number of Seeds | Mostly single seeded pods, some pods double seeded |
| Seed Color | Reddish brown |
| Seed Weight (average calculated from 1000 seed weight) | 0.172 g |
| Seed Shape | Intermediate (between angular and pea-shaped) |
| Seed Surface | Some roughness |
| Seed Ribbing | Weak |
| Seed Protein Content | 24% |

Overview of the Variety 'NC-009'

Figure 9A:
FIGS. 9A-9B show seeds and plants of chickpea variety 'NC-009'.
Figure 9B:

Chickpea variety 'NC-009' is a genetically unique chickpea plant exhibiting medium brown seeds and a seed protein content of 30%. Chickpea variety 'NC-009' is a recombinant inbred line resulting from a controlled cross followed by numerous generations of self-pollination and was selected for its seed protein content. Chickpea variety 'NC-009' is propagated through self-pollination. FIG. 9A shows seeds of chickpea variety 'NC-009'. FIG. 9B shows plants of the chickpea variety 'NC-009', including the leaves and pods of the variety, and illustrates the intermediate (between prostrate and upright) growth habit of the variety.

The variety 'NC-009' has shown uniformity and stability for the traits, within the limits of environmental influence for the traits. It has been self-pollinated a sufficient number of generations with careful attention to uniformity of plant type. It has been increased with continued observation for uniformity. No variant traits have been observed or are expected in variety 'NC-009'.

Objective Description of the Variety 'NC-009'

Table 9 provides a summary of chickpea variety 'NC-009' plant characteristics. These characteristics were observed in plants of the variety that were planted between early April through early May near Davis, California, U.S.A. Trait measurements, color descriptions, and other phenotypical descriptions may deviate from the stated values and descriptions depending upon variation in environmental, seasonal, climatic, and cultural conditions. 'NC-009' has not been observed under all possible environmental conditions. The indicated protein content represents an average across five field trials including 8 data points. The protein data was collected using multiple protein test methods and moisture values, and then extrapolated for averaging purposes. Those of skill in the art will recognize that these are typical values that may vary due to environment and that other values that are substantially equivalent are within the scope of the invention. As used herein, "a chickpea plant having all the physiological and morphological characteristics of chickpea variety 'NC-009'" is a plant having the characteristics set forth in Table 9 when grown in the same environmental conditions.

TABLE 9

| Characteristic | Value |
|---|---|
| Plant Morphology and Growth | |
| Plant Height | 300 mm |
| Growth Habit | Intermediate (between prostrate and upright) |
| Time to Dry Seed Maturity | 99 days |
| Method of Propagation | Self-pollination |
| Time of Beginning of Flowering | 40 days |
| Flower Characteristics | |
| Flower Color | White |
| Pod and Seed Characteristics | |
| Pod: Number of seeds | Mostly single seeded pods, some pods double seeded |
| Seed Color | Medium brown |
| Seed Weight (average calculated from 1000 seed weight) | 0.116 g |
| Seed Shape | Intermediate (between angular and pea-shaped) |
| Seed Surface | Some roughness |
| Seed Ribbing | Medium |
| Seed Protein Content | 30% |

Further Embodiments

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Any DNA sequences, whether from a different species or from the same species, which are introduced into the genome using transformation or various breeding methods, are referred to herein collectively as "transgenes." Numerous methods for producing transgenic plants have been developed, and the present invention, in particular embodiments, also relates to transformed versions of the claimed line.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

Plant transformation involves the construction of an expression vector that will function in plant cells. Such a vector contains DNA that contains a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed chickpea plants using transformation methods as described below to incorporate transgenes into the genetic material of the chickpea plant(s).

Gene Conversions

When the terms chickpea variety, plant, hybrid, cultivar, or line are used in the context of the present invention, this also includes any single gene conversions. The term "single gene converted plant" as used herein refers to those chickpea plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present invention to improve or introduce a characteristic into the line. The term "backcrossing" as used herein refers to the repeated crossing of a hybrid progeny back to one of the parental chickpea plants for that line, backcrossing 1, 2, 3, 4, 5, 6, 7, 8, or more times to the recurrent parent. The parental chickpea plant which contributes the gene for the desired characteristic is termed the nonrecurrent or donor parent. This terminology refers to the fact that the nonrecurrent parent is used one time in the backcross protocol and therefore does not recur. The parental chickpea plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a chickpea plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Examples of single gene traits include but are not limited to, male sterility, modified fatty acid metabolism, modified carbohydrate metabolism, herbicide resistance, nematode resistance, resistance for bacterial, fungal, or viral disease, insect resistance, enhanced nutritional quality, industrial usage, yield stability and yield enhancement. These genes are generally inherited through the nucleus. Several of these single gene traits are described in U.S. Pat. Nos. 5,777,196, 5,948,957 and 5,969,212, the disclosures of which are specifically hereby incorporated by reference.

In some embodiments of the present invention, agronomic genes can be expressed in transformed plants of the chickpea varieties described herein to confer value-added traits thereto. More particularly, plants can be genetically engineered to express various phenotypes of agronomic interest. Exemplary genes implicated in this regard include, but are not limited to, genes that confer resistance to pests, disease, insects, or herbicides; and genes that modify fatty acid, amino acid, or carbohydrate metabolism.

Genes that confer resistance to pests or disease include, but are not limited to, cloned resistance genes (e.g. Jones et al., *Science,* 266:7891, 1994; Martin et al., *Science,* 262:1432, 1993; and Mindrinos et al., *Cell,* 78 (6): 1089-1099, 1994), genes encoding viral-invasive proteins or complex toxins derived therefrom, genes encoding virus-specific antibodies, genes encoding viral coat proteins (e.g. Beachy et al., *Ann. Rev. Phytopathol.,* 28:451, 1990), genes that modulate the systemic acquired resistance (SAR) or pathogenesis related (PR) genes (e.g. Ryals et al., *Plant Cell,* 8:1809-1819, 1996), ribosome-inactivating genes (e.g. Logemann et al., *Biotechnology,* 10:305, 1992), plant defensin genes (e.g. Thomma et al., *Planta,* 216:193-202, 2002), and the like.

Genes that confer resistance to insects include, but are not limited to, *Bacillus thuringiensis* endotoxin genes (e.g. Geiser et al., *Gene,* 48 (1): 109-118, 1986), lectins (e.g. Van Damme et al. *Plant Molec. Biol.,* 24:25, 1994), genes encoding vitamin-binding proteins such as avidin (e.g. PCT Application No. US93/06487), genes encoding enzyme inhibitors such as protease, proteinase or amylase inhibitors (e.g. Abe et al. *J. Biol. Chem.,* 262:16793, 1987; Huub et al. *Plant Molec. Biol.,* 21:985, 1993; Sumitani et al. *Biosci. Biotech. Biochem.,* 57:1243, 1993), genes encoding insect-specific hormones or pheromones (e.g. Gade and Goldsworthy (Eds. *Physiological System in Insects,* Elsevier Academic Press, Burlington, Mass., 2007), genes encoding insect-specific antibodies or immunotoxin derived therefrom (e.g. Taylor et al. Seventh Inn Symposium on Molecular Plant-Microbe Interactions, Edinburgh, Scotland, Abstract W97, 1994), and genes encoding developmental-arrestive proteins.

Genes that confer resistance to herbicides include, but are not limited to, mutant ALS and AHAS enzymes (e.g. Lee et al., *EMBO J.,* 7:1241, 1988; Gleen et al., *Plant Molec. Biology,* 18:1185-1187, 1992; and Miki et al., *Theor. Appl. Genet.,* 80:449, 1990); mutant aroA genes (e.g. U.S. Pat. No. 4,769,061); hygromycin B phosphotransferase genes (e.g. Penaloza-Vazquez et al., *Plant Cell Reports,* 14:482-487, 1995); glutamine synthetase genes (e.g. Penaloza-Vazquez et al., *Plant Cell Reports,* 14:482-487, 1995; European Patent Application No. 0 333 033; U.S. Pat. No. 4,975,374); phosphinothricin-acetyltransferase genes (e.g. European Patent Application No. 0 242 246); chimeric bar genes coding for phosphinothricin acetyl transferase activity (e.g. DeGree F. et al., *Biotechnology,* 7:61, 1989); Acct-S1, Acct-S2 and Acct-S3 genes (e.g. Marshall et al., *Theor. Appl. Genet.,* 83:4:35, 1992); genes conferring resistance to a herbicide that inhibits photosynthesis (e.g. triazine and benzonitrile) such as psbA genes (e.g. Przibila et al., *Plant Cell,* 3:169, 1991), gs+ genes, and nitrilase genes (e.g. U.S. Pat. No. 4,810,648); glutathione S-transferase genes (e.g. Hayes et al., Biochem. J., 285 (Pt 1): 173-180, 1992); PPO-inhibitor resistant PPO genes (e.g. Patzoldt et al., *PNAS,* 103(33):12329-2334, 2006); glutathione reductase genes (e.g. Foyer et al., *Plant Physiol.,* 109:1047-1057, 1995); 2,4-D monooxygenase genes (e.g. Bayley et al., *Theor. Appl. Genet.,* 83:645-649, 1992); and dicamba monooxygenase genes (e.g. U.S. Pat. App. Pub. No. 20030135879).

Genes that modify fatty acid metabolism include, but are not limited to, stearyl-ACP desaturase genes (e.g. Knutzon et al., *Proc. Natl. Acad. Sci. USA,* 89:2624, 1992) and fatty acid desaturase genes (e.g. McDonough et al., *J. Biol. Chem.,* 267 (9): 5931-5936, 1992; Fox et al., *Proc. Natl. Acad. Sci. USA,* 90 (6): 2486-2490, 1993; Reddy et al., *Plant Mol. Biol.,* 22 (2): 293-300, 1993; Arondel et al. *Science,* 258 (5086): 1353-1355, 1992; PCT Application Publ. No. WO 91/13972; European Patent Application Publ. No. EP 0616644; U.S. Pat. No. 7,622,632; EP U.S. Pat. No. 1,656, 449; U.S. Pat. App. Pub. No. 2008-0260929). Genes that modify carbohydrate metabolism include, but are not limited to, genes encoding enzymes that alter the branching pattern of starch (e.g. Shiroza et al., *J. Bacteriol.,* 170:810, 1988; Steinmetz et al., *Mol. Gen. Genet.,* 20:220, 1985; Pen et al., *Biotechnology,* 10:292, 1992; Elliot et al., *Plant Molec. Biol.,* 21:515, 1993; Sergaard et al., *J. Biol. Chem.,* 268: 22480, 1993; Fisher et al., *Plant Physiol.,* 102:1045, 1993) (maize endosperm starch branching enzyme II).

Tissue Culture

Further reproduction of the varieties can occur by tissue culture and regeneration. Tissue culture of various tissues of chickpea and regeneration of plants therefrom is well known and widely published. For example, reference may be had to: Kartha, et al (1981) Plant regeneration from meristems of grain legumes: soybean, cowpea, peanut, chickpea, and bean. *Canadian Journal of Botany.* 59(9):1671-1679; Clarke et al. (2006) Embryo rescue and plant regeneration in vitro of selfed chickpea (*Cicer arietinum* L.) and its wild annual relatives. *Plant Cell Tiss Organ Cult* 85, 197-204; Riazuddin et al. (1988) Establishment of callus-tissue culture and the induction of organogenesis in chickpea. *Pakistan Journal of Agricultural Research* Vol. 9 No. 3 339-345; Rao and Naidu (1989). A tissue culture derived pesticide tolerant line of chickpea (*Cicer arietinum* L.). *Proc. Indian Acad. Sci. (Plant Sci.)* 99, 523-527; and Maiti and Ebeling (2001) *Advances in Chickpea Science.* Science Publishers, U.S.A. It is clear from the literature that these methods of obtaining plants are "conventional" in the sense that they are routinely successfully used. Thus, another aspect of this invention is to provide cells which upon growth and differentiation produce chickpea plants having the physiological and morphological characteristics of chickpea variety 'NC-001', 'NC-002', 'NC-003', 'NC-004', 'NC-005', 'NC-006', 'NC-007', 'NC-008', or 'NC-009'.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

Commodity Plant Products

In one aspect, the present invention provides a commodity plant product produced from seeds of chickpea variety 'NC-001', 'NC-002', 'NC-003', 'NC-004', 'NC-005', 'NC-006', 'NC-007', 'NC-008', or 'NC-009', or from seeds of a chickpea plant having all the morphological and physiological characteristics of chickpea variety 'NC-001', 'NC-002', 'NC-003', 'NC-004', 'NC-005', 'NC-006', 'NC-007', 'NC-008', or 'NC-009'. A commodity plant product encompasses any product derived from a plant, or a plant part thereof, which is used as a commodity material in industry or food production. For example, commodity plant products of chickpeas may include protein isolate, protein concentrate, texturized protein, meal, flour, starch, fiber, or oil derived from chickpeas.

In some embodiments, the commodity plant product of the present invention is a chickpea meal or a chickpea flour. The chickpea meal or chickpea flour may be produced by any means known in the art. For example, the chickpea meal or flour may be produced by soaking whole chickpeas in water for up to 24 hours, wet milling the whole chickpeas to form a paste, and drying the paste to produce a chickpea meal or flour. Alternatively, the chickpea meal or flour may be produced by dry milling dried chickpeas to a course, fine, or intermediate consistency. Either hulled or de-hulled chickpeas can be used in the production of the chickpea meal or chickpea flour. These methods may be used to produce a course chickpea meal with a particle size of greater than 1000 microns, or may be used to produce a fine chickpea flour with a particle size of less than 1000, less than 400, or less than 200 microns. The chickpea meal or flour may be dried, for example, to a moisture content of 15% or less. The chickpea meal or chickpea flour may consist of whole ground chickpeas and, therefore, have a nutritional content similar to that of the dried chickpeas from which it was made. Alternatively, additives may be added in the production of the chickpea meal or flour to alter the nutritional content compared to the whole chickpeas. The chickpea meal or flour may have a protein content of as low as 5% or exceeding 30%.

In other embodiments, the commodity plant product of the present invention is a chickpea protein isolate or a chickpea protein concentrate. The chickpea protein isolate or a chickpea protein concentrate may be produced by any means known in the art for producing plant-derived protein isolates and concentrates. Methods of producing protein isolates and concentrates from chickpeas and other legumes are well known in the art. For example, see U.S. Pat. Nos. 8,142,832, 8,557,321, 8,563,071, 9,370,200, 10,143,226, 10,390,544, and 10,834,941; and U.S. Pat. App. Pub. Nos. 2020-0390131, 2016-0309743, and 2021-0051975. Generally, chickpea protein isolates and concentrates have a protein content of at least about 70% and may have a protein content exceeding 95%.

In some embodiments, the commodity plant product of the present invention is a chickpea oil. Chickpea oil may be produced by any means known in the art for vegetable oils, especially those used in the production of legume oils. Methods for extracting and processing vegetable oils have been developed over decades and are readily available to one skilled in the art. For example, see Dutton (1981) History of the development of soy oil for edible uses. *J Am Oil Chem Soc* 58, 234; Lou et al. (2010) Improved extraction of oil from chickpea under ultrasound in a dynamic system. *Journal of Food Engineering*, 98:1, pp 13-18, Hamm et al. (Eds) (2013) *Edible Oil Processing*, $2^{nd}$ Edition, Wiley-Blackwell; Gupta (2017) *Practical Guide to Vegetable Oil Processing*, Academic Press; Chemat (2017) *Edible Oils: Extraction, Processing, and Applications*, CRC Press.

In some embodiments, the commodity plant product of the present invention is a chickpea starch. Chickpea starch may be produced by any means known in the art for making food starches, especially those used in the production of pulse or legume starches. Methods for extracting, refining, modifying, and otherwise processing food starches have been developed over decades and are readily available to one skilled in the art. For example, see Radley (1976) *Starch Production Technology*, Applied Science Publishers; Ratnayake and Jackson (2003) STARCH: Sources and Processing, *Encyclopedia of Food Sciences and Nutrition*, $2^{nd}$ Edition, Academic Press; Panda (2004) *The Complete Technology Book on Starch and Its Derivatives*, Asia Pacific Business Press; BeMiller and Whistler (2009), *Starch: Chemistry and Technology*, $3^{rd}$ Edition, Academic Press; and U.S. Pat. No. 5,364,471. In some embodiments, chickpea starch production may comprise milling (e.g. grinding), washing, sieving, and/or drying chickpea seeds, chickpea flour, or other chickpea material. In certain embodiments, chickpea starch is produced as a by-product of chickpea protein isolate or protein concentrate production.

In some embodiments, the commodity plant product of the present invention is a chickpea fiber. Chickpea fiber may be produced by any means known in the art for producing dietary fiber, especially those used in the recovery and/or production of pulse or legume fibers. Methods for producing fiber have are well-developed and are readily available to one skilled in the art. For example, see Kozlowski (2012) *Handbook of Natural Fibers*, $1^{st}$ Edition, Volume 2: Processing and Applications, Woodhead Publishing; Galanakis (2019) *Dietary Fiber: Properties, Recovery, and Applications*, $1^{st}$ Edition, Academic Press; Hussain et al. (2020) Dietary Fiber from Underutilized Plant Sources—A Positive Approach for Valorization of Fruit and Vegetable Wastes. *Sustainability* 12, 5401; and Mondal (2021) *Fundamentals of Natural Fibres and Textiles*, $1^{st}$ Edition, Woodhead Publishing. In certain embodiments, chickpea fiber is produced as a by-product of chickpea processing, canning, protein isolate, or protein concentrate production.

In some embodiments, the commodity plant product of the present invention can be used as an ingredient substitutes for food products such as, but not limited to, whey protein, eggs, dairy (e.g., milk, dairy desserts, beverages, ice cream, or any combination thereof), spreads and dressings (e.g. mayonnaise, sauces, or any combination thereof), baked goods (e.g. gluten free bread, crackers, or any combination thereof), pasta (e.g. gluten-free pasta), beverages (e.g. shakes, fruit smoothies, or any combination thereof), snacks (e.g. energy bars), meat substitutes (e.g. burgers, patties, sausages, meatballs, ground meat, sliced meat, etc.), baby formula, or food product known in the art. Examples of foods incorporating chickpea commodity plant products, and methods of making thereof, are described in and U.S. Pat. Nos. 10,039,306, 10,390,544, and U.S. Pat. App. Pub. Nos. 2018-0042278, 2019-0045809, 2020-0390131, 2021-0022352, 2021-0051975, 2019-0037893.

Additional Breeding Methods

The invention is also directed to methods for producing a chickpea plant by crossing a first parent chickpea plant with a second parent chickpea plant where the first or second parent chickpea plant is a chickpea plant of variety 'NC-001', 'NC-002', 'NC-003', 'NC-004', 'NC-005', 'NC-006', 'NC-007', 'NC-008', or 'NC-009'. Further, both first and second parent chickpea plants can come from chickpea variety 'NC-001', 'NC-002', 'NC-003', 'NC-004', 'NC-005', 'NC-006', 'NC-007', 'NC-008', or 'NC-009'. Thus, any such methods using chickpea variety 'NC-001', 'NC-002', 'NC-003', 'NC-004', 'NC-005', 'NC-006', 'NC-007', 'NC-008', or 'NC-009' are part of the invention: selfing, backcrosses, hybrid production, crosses to populations, and the like. All plants produced using chickpea variety 'NC-001', 'NC-002', 'NC-003', 'NC-004', 'NC-005', 'NC-006', 'NC-007', 'NC-008', or 'NC-009' as at least one parent are within the scope of this invention, including those developed from varieties derived from chickpea variety 'NC-001', 'NC-002', 'NC-003', 'NC-004', 'NC-005', 'NC-006', 'NC-007', 'NC-008', or 'NC-009'. Advantageously, this chickpea variety could be used in crosses with other, different, chickpea plants to produce the first generation (F$_1$) chickpea hybrid seeds and plants with superior characteristics. The varieties of the invention can also be used for transformation where exogenous genes are introduced and expressed by the varieties of the invention. Genetic variants created either through traditional breeding methods using chickpea variety 'NC-001', 'NC-002', 'NC-003', 'NC-004', 'NC-005', 'NC-006', 'NC-007', 'NC-008', or 'NC-009', or through transformation of variety 'NC-001', 'NC-002', 'NC-003', 'NC-004', 'NC-005', 'NC-006', 'NC-007', 'NC-008', or 'NC-009' by any of a number of protocols known to those of skill in the art are intended to be within the scope of this invention.

The following describes breeding methods that may be used with chickpea variety 'NC-001', 'NC-002', 'NC-003', 'NC-004', 'NC-005', 'NC-006', 'NC-007', 'NC-008', or 'NC-009' in the development of further chickpea plants. One such embodiment is a method for developing variety 'NC-001', 'NC-002', 'NC-003', 'NC-004', 'NC-005', 'NC-006', 'NC-007', 'NC-008', or 'NC-009' progeny chickpea plants in a chickpea plant breeding program, by: obtaining the chickpea plant, or a plant part thereof, of variety 'NC-001', 'NC-002', 'NC-003', 'NC-004', 'NC-005', 'NC-006', 'NC-007', 'NC-008', or 'NC-009', utilizing said plant or plant part as a source of breeding material, and selecting a chickpea variety 'NC-001', 'NC-002', 'NC-003', 'NC-004', 'NC-005', 'NC-006', 'NC-007', 'NC-008', or 'NC-009' progeny plant with molecular markers in common with variety 'NC-001', 'NC-002', 'NC-003', 'NC-004', 'NC-005', 'NC-006', 'NC-007', 'NC-008', or 'NC-009' and/or with morphological and/or physiological characteristics selected from the characteristics listed in the section entitled "Objective Description of the Variety 'NC-001'", "Objective Description of the Variety 'NC-002'", "Objective Description of the Variety 'NC-003'", "Objective Description of the Variety 'NC-004'", "Objective Description of the Variety 'NC-005'", "Objective Description of the Variety 'NC-006'", "Objective Description of the Variety 'NC-007'", "Objective Description of the Variety 'NC-008'", or "Objective Description of the Variety 'NC-009'". Breeding steps that may be used in the chickpea plant breeding program include pedigree breeding, backcrossing, mutation breeding, and recurrent selection. In conjunction with these steps, techniques such as genetic marker enhanced selection (for example, RFLP, SSR or SNP markers), and the making of double haploids may be utilized.

Another method involves producing a population of chickpea variety 'NC-001', 'NC-002', 'NC-003', 'NC-004', 'NC-005', 'NC-006', 'NC-007', 'NC-008', or 'NC-009' progeny chickpea plants, by crossing variety 'NC-001', 'NC-002', 'NC-003', 'NC-004', 'NC-005', 'NC-006', 'NC-007', 'NC-008', or 'NC-009' with another chickpea plant, thereby producing a population of chickpea plants, which, on average, derive 50% of their alleles from chickpea variety 'NC-001', 'NC-002', 'NC-003', 'NC-004', 'NC-005', 'NC-006', 'NC-007', 'NC-008', or 'NC-009'. A plant of this population may be selected and repeatedly selfed or sibbed with a chickpea variety resulting from these successive filial generations. One embodiment of this invention is the chickpea variety produced by this method and that has obtained at least 50% of its alleles from chickpea variety 'NC-001', 'NC-002', 'NC-003', 'NC-004', 'NC-005', 'NC-006', 'NC-007', 'NC-008', or 'NC-009'. One of ordinary skill in the art of plant breeding would know how to evaluate the traits of two plant varieties to determine if there is no significant difference between the two traits expressed by those varieties. For example, see Fehr, *Principles of Cultivar Development*, (1987). Thus the invention includes chickpea variety 'NC-001', 'NC-002', 'NC-003', 'NC-004', 'NC-005', 'NC-006', 'NC-007', 'NC-008', or 'NC-009' progeny chickpea plants containing a combination of at least two variety 'NC-001', 'NC-002', 'NC-003', 'NC-004', 'NC-005', 'NC-006', 'NC-007', 'NC-008', or 'NC-009' traits selected from those listed in the section entitled "Objective Description of the Variety 'NC-001'", "Objective Description of the Variety 'NC-002'", "Objective Description of the Variety 'NC-003'", "Objective Description of the Variety 'NC-004'", "Objective Description of the Variety 'NC-005'", "Objective Description of the Variety 'NC-006'". "Objective Description of the Variety 'NC-007'", "Objective Description of the Variety 'NC-008'", or "Objective Description of the Variety 'NC-009'", or the variety 'NC-001', 'NC-002', 'NC-003', 'NC-004', 'NC-005', 'NC-006', 'NC-007', 'NC-008', or 'NC-009' combination of traits listed in the Summary of the Invention, so that said progeny chickpea plant is not significantly different for said traits than chickpea variety 'NC-001', 'NC-002', 'NC-003', 'NC-004', 'NC-005', 'NC-006', 'NC-007', 'NC-008', or 'NC-009' as determined at the 5% significance level when grown in the same environmental conditions. Using techniques described herein, molecular markers may be used to identify said progeny plant as a chickpea variety 'NC-001', 'NC-002', 'NC-003', 'NC-004', 'NC-005', 'NC-006', 'NC-007', 'NC-008', or 'NC-009' progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Traits that may be evaluated in the progeny of chickpea varieties 'NC-001', 'NC-002', 'NC-003', 'NC-004', 'NC-005', 'NC-006', 'NC-007', 'NC-008', and 'NC-009' include, for example, seed size, seed weight, number of seeds per pod, seed yield, seed coloration, seed coat characteristics (e.g. thickness), seed protein quantity, seed protein content, seed protein composition, seed protein functional properties, other seed chemistries, overall seed nutritional content, the presence or amount of pro- and anti-nutritional factors, degree of nodulation and/or nitrogen fixation, drought tolerance, heat tolerance, tolerance to aluminum in acid soils, flowering time, time to maturity, plant architecture, yield, agronomic quality, and the like. One exemplary trait of interest is seed protein content. Seed protein content is determined using biochemical assays including, but not limited to, combustion elemental analysis methods (e.g. the Total Nitrogen Combustion Method, also known as the Dumas method) or methods using fluorescent or spectrophotometric detection. Exemplary biochemical assays for determining protein content are described in Hayes (2020. Measuring protein content in food: an overview of methods. Foods 9:1340). Total protein is typically expressed relative to mature seed weight, with correction for seed coat, though it may also be expressed on a fresh weight basis or without correction for seed coat.

Progeny of chickpea variety 'NC-001', 'NC-002', 'NC-003', 'NC-004', 'NC-005', 'NC-006', 'NC-007', 'NC-008', or 'NC-009' may also be characterized through their filial relationship with chickpea variety 'NC-001', 'NC-002', 'NC-003', 'NC-004', 'NC-005', 'NC-006', 'NC-007', 'NC-008', or 'NC-009', as for example, being within a certain number of breeding crosses of chickpea variety 'NC-001', 'NC-002', 'NC-003', 'NC-004', 'NC-005', 'NC-006', 'NC-007', 'NC-008', or 'NC-009'. A breeding cross is a cross made to introduce new genetics into the progeny, and is distinguished from a cross, such as a self or a sib cross, made to select among existing genetic alleles. The lower the number of breeding crosses in the pedigree, the closer the relationship between chickpea variety 'NC-001', 'NC-002', 'NC-003', 'NC-004', 'NC-005', 'NC-006', 'NC-007', 'NC-008', or 'NC-009' and its progeny. For example, progeny produced by the methods described herein may be within 1, 2, 3, 4, or 5 breeding crosses of chickpea variety 'NC-001', 'NC-002', 'NC-003', 'NC-004', 'NC-005', 'NC-006', 'NC-007', 'NC-008', or 'NC-009'.

Another method involves crossing a plant of one of the chickpea varieties 'NC-001', 'NC-002', 'NC-003', 'NC-004', 'NC-005', 'NC-006', 'NC-007', 'NC-008', or 'NC-009' with a plant of another of the chickpea varieties 'NC-001', 'NC-002', 'NC-003', 'NC-004', 'NC-005', 'NC-006', 'NC-007', 'NC-008', or 'NC-009', and selecting a progeny plant having a quantitative trait value that surpasses both parents. The progeny plant may have a quantitative trait value that is higher than both parents (e.g. a protein quantity exceeding that of both parents) or that is lower than both parents (e.g. a quantity of an anti-nutritional factor that is less than that of both parents). Such traits are the product of combining the genetic capacities inherent to the parental plants of 'NC-001', 'NC-002', 'NC-003', 'NC-004', 'NC-005', 'NC-006', 'NC-007', 'NC-008', and 'NC-009', and are thus within the scope of the present invention. The progeny of a cross of two of the varieties 'NC-001', 'NC-002', 'NC-003', 'NC-004', 'NC-005', 'NC-006', 'NC-007', 'NC-008', or 'NC-009' may surpass both of the parent varieties in any plant trait including, but not limited to, seed size, seed weight, number of seeds per pod, seed yield, seed coloration, seed coat characteristics (e.g. thickness), seed protein quantity, seed protein content, seed protein composition, seed protein functional properties, other seed chemistries, overall seed nutritional content, the presence or amount of pro- and anti-nutritional factors, degree of nodulation and/or nitrogen fixation, drought tolerance, heat tolerance, tolerance to aluminum in acid soils, flowering time, time to maturity, plant architecture, yield, agronomic quality, and the like.

As used herein, the term "plant" includes plant cells, plant protoplasts, plant cell tissue cultures from which chickpea plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like. As used herein, "plant part" includes seeds, pollen grains, ovules, protoplasts, cells, embryos, cotyledons, hypocotyls, meristems, roots, pistils, anthers, flowers, stems, pods, leaves, petioles, and any other part of a chickpea plant known in the art.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

Chickpea Variety 'NC-001'

A deposit of at least 625 seeds of the chickpea variety 'NC-001' was made with the American Type Culture Collection, (ATCC), ATCC Patent Depository, 10801 University Boulevard, Manassas, Virginia, 20110, USA, and assigned ATCC Number PTA-127935. The seeds deposited with the ATCC on Sep. 19, 2025 were obtained from the seed of the variety maintained by NuCicer, Inc., having an address at 7661 Becker Road, Davis, California, 95618, U.S.A. since prior to the filing date of the application. Access to this deposit will be available during the pendency of this application to persons determined by the Commissioner of Patents and Trademarks to be entitled thereto under 37 C.F.R. § 1.14 and 35 U.S.C. § 122. Upon issuance, the Applicant will make the deposit available to the public consistent with all of the requirements of 37 C.F.R. § 1.801-1.809. This deposit of the chickpea variety 'NC-001' will be maintained in the ATCC, which is a public depository, for a period of 30 years, or at least 5 years after the most recent request for a sample of the deposit, or for the effective life of the patent, whichever is longer, and will be replaced if it becomes nonviable during that period. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

What is claimed is:

1. A chickpea seed designated as 'NC-001', representative sample of seed having been deposited under ATCC Accession Number PTA-127935.

2. A chickpea plant produced by growing the seed of claim 1.

3. A plant part from the plant of claim 2.

4. The plant part of claim 3, wherein said plant part is a pollen grain, ovule, protoplast, cell, embryo, cotyledon, hypocotyl, meristem, root, pistil, anther, flower, stem, pod, leaf, petiole, or a portion thereof.

5. The plant part of claim 3, wherein said plant part is a seed.

6. A chickpea plant having all the physiological and morphological characteristics of the chickpea plant of claim 2.

7. A plant part from the plant of claim 6.

8. The plant part of claim 7, wherein said plant part is a pollen grain, ovule, protoplast, cell, embryo, cotyledon, hypocotyl, meristem, root, pistil, anther, flower, stem, pod, leaf, petiole, or a portion thereof.

9. The plant part of claim 7, wherein said plant part is a seed.

10. A tissue culture of the plant of claim 2.

11. A chickpea plant regenerated from the tissue culture of claim 10, wherein the plant has all of the morphological and physiological characteristics of a chickpea plant produced by growing seed designated as 'NC-001' having ATCC Accession Number PTA-127935.

12. A method of making chickpea seeds, said method comprising crossing the plant of claim 2 with another chickpea plant and harvesting seed therefrom.

13. A method of making a chickpea variety designated as 'NC-001', said method comprising selecting seeds from the cross of one 'NC-001' plant with another 'NC-001' plant, a sample of 'NC-001' chickpea seed having been deposited under ATCC Accession Number PTA-127935.

14. A method of producing a commodity plant product, comprising obtaining the plant of claim 2 or a plant part thereof and producing said commodity plant product therefrom.

15. The method of claim 14, wherein the plant part is a seed.

16. The method of claim 14, wherein the commodity plant product is a protein isolate, a protein concentrate, a texturized protein product, a meal, a flour, a starch, a fiber or an oil.

17. A commodity plant product produced according to the method of claim 14.

* * * * *